United States Patent [19]

Davies et al.

[11] Patent Number: 4,997,840

[45] Date of Patent: Mar. 5, 1991

[54] QUINOLONE SULPHONATES HAVING ANTIHYPERTENSIVE ACTIVITY

[75] Inventors: Roy V. Davies; Michael D. Brown; Nicholas J. Holman, all of Nottinghamshire, England

[73] Assignee: The Boots Company, PLC, Nottingham, England

[21] Appl. No.: 399,459

[22] PCT Filed: Feb. 9, 1989

[86] PCT No.: PCT/GB89/00126

§ 371 Date: Sep. 1, 1989

§ 102(e) Date: Sep. 1, 1989

[87] PCT Pub. No.: WO89/07593

PCT Pub. Date: Aug. 24, 1989

[30] Foreign Application Priority Data

Feb. 22, 1988 [GB] United Kingdom ............... 8804016

[51] Int. Cl.$^5$ ................... A61K 31/47; C07D 215/22
[52] U.S. Cl. .................... 514/312; 546/155
[58] Field of Search ............... 514/312; 546/155

[56] References Cited

U.S. PATENT DOCUMENTS

| | | | |
|---|---|---|---|
| 3,718,653 | 2/1973 | Hamer | 514/314 |
| 4,192,873 | 3/1980 | Ferrini et al. | |
| 4,263,455 | 4/1981 | Ferrini et al. | 564/305 |
| 4,302,460 | 11/1981 | Davies et al. | 514/312 |
| 4,442,109 | 4/1984 | Davies | 514/312 |
| 4,447,435 | 5/1984 | Davies | 514/312 |
| 4,515,796 | 5/1985 | Robertson | 514/303 |
| 4,552,884 | 11/1985 | Sim et al. | 514/312 |
| 4,578,387 | 3/1986 | Spitzer | 514/249 |
| 4,582,837 | 4/1986 | Hauel et al. | 514/303 |
| 4,591,600 | 5/1986 | Creuzet et al. | 514/456 |
| 4,600,788 | 7/1986 | Creuzet et al. | 549/403 |
| 4,636,575 | 1/1987 | Kirchmayr | 546/155 |
| 4,656,171 | 4/1987 | Austel et al. | 514/250 |
| 4,659,718 | 4/1987 | Davies et al. | 514/312 |
| 4,670,438 | 6/1987 | Austel et al. | 514/249 |
| 4,670,445 | 6/1987 | Spitzer | 514/300 |
| 4,696,931 | 9/1987 | Hauel et al. | 514/261 |
| 4,746,658 | 5/1988 | Austel et al. | 514/248 |
| 4,772,614 | 9/1988 | Davies et al. | 514/312 |
| 4,855,291 | 8/1989 | Davies | 514/312 |

FOREIGN PATENT DOCUMENTS

| | | |
|---|---|---|
| 5154385 | 6/1986 | Australia . |
| 5893286 | 12/1987 | Australia . |
| 0155094 | 2/1985 | European Pat. Off. . |
| 0330340 | 8/1989 | European Pat. Off. ............ 546/195 |

89/04827 6/1989 PCT Int'l Appl. .

OTHER PUBLICATIONS

Chemical and Pharmaceutical Bulletin, vol. 28 (2), 493-499 (1980)–Shichiri et al.
Chemical Abstracts, vol. 61 (1964), 3067h–Hamana & Funakoshi.
Chemical Abstracts, vol. 86 (1977): 188613e–Pileni & Santus.
Journal of the American Chemical Society, vol. 97(24), 7191-7193 (1975)–Saito et al.
Journal of the Chemical Society (1980), 2738-2742–Albini et al.
Australian Journal of Chemistry, 1974, vol. 27, 537-42–Evans & Eastwood.
Derwent Abstract No. 85-029006/05–Hamari Yukuhin Kogy KK.
Derwent Abstract No. 85-200345/33–Hamari Yukuhin Kogy KK.
Derwent Abstract No. 86-199698/31–Hamari Yukuhin Kogy KK.

Primary Examiner—Donald G. Daus
Attorney, Agent, or Firm—Armstrong, Nikaido, Marmelstein, Kubovcik & Murray

[57] ABSTRACT

Quinolone sulphonates of formula I

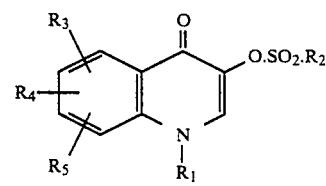

in which $R_1$ is lower alkyl; $R_2$ is lower alkyl; and $R_3$, $R_4$ and $R_5$, which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo, have antihypertensive activity.

Processes for preparing compounds of formula I and pharmaceutical compositions containing them are described.

Compounds of formula I are also indicated for use in the treatment of heart failure and ischaemic heart disease.

22 Claims, No Drawings

QUINOLONE SULPHONATES HAVING ANTIHYPERTENSIVE ACTIVITY

This invention relates to novel quinolone derivatives having therapeutic activity useful in treating cardiovascular diseases, therapeutic compositions containing the novel quinolone derivatives and to processes for preparing the novel quinolone derivatives.

The present invention provides quinolone derivatives of the formula I

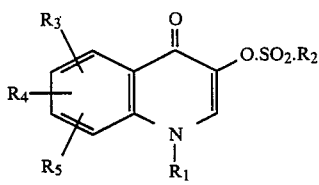

in which $R_1$ is lower alkyl; $R_2$ is lower alkyl; and $R_3$, $R_4$ and $R_5$, which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo.

The term 'lower' as used herein signifies a group which may be straight or branched and which has 1 to 6 carbon atoms preferably 1 to 4 carbon atoms. Lower alkyl substituents include, for example, methyl, ethyl, propyl, isopropyl, butyl, isobutyl. pentyl and hexyl. Lower alkoxy substituents include, for example, methoxy, ethoxy, propoxy, isopropoxy, butoxy and isobutoxy. Lower alkylthio substituents include, for example, methylthio, ethylthio, propylthio, isopropylthio, butylthio and isobutylthio.

The term 'halo' signifies fluoro, chloro or bromo. Halogenated lower alkyl and halogenated lower alkoxy substituents are preferably fluorinated and examples of such groups are trifluoromethyl, trifluoromethoxy and 2,2,2-trifluoroethoxy.

When at least one of $R_3'$ $R_4$ and $R_5$ is substituted phenyl the substituents may be selected from lower alkyl such as methyl or ethyl, lower alkoxy such as methoxy or ethoxy and halo such as chloro or fluoro.

In preferred compounds of formula I, $R_1$ is lower alkyl; $R_2$ is lower alkyl; $R_3$ and $R_4$ are as hereinbefore defined; and $R_5$ is hydrogen.

Particularly preferred compounds of formula I are those in which $R_1$ is alkyl having 1 to 4 carbon atoms; $R_2$ is alkyl having 1 to 4 carbon atoms; $R_3$ and $R_4$, which may be the same or different, are hydrogen, lower alkyl having 1 to 4 carbon atoms, lower alkoxy having 1 to 4 carbon atoms, lower alkylthio having 1 to 4 carbon atoms, lower alkylsulphinyl having 1 to 4 carbon atoms, lower alkylsulphonyl having 1 to 4 carbon atoms, halo, fluorinated lower alkyl having to 4 carbon atoms, fluorinated lower alkoxy having 1 to 4 carbon atoms, cyano, phenyl or phenyl substituted by 1 or 2 groups independently selected from alkyl having 1 to 4 carbon atoms, alkoxy having 1 to 4 carbon atoms and halo; and $R_5$ is hydrogen.

More particularly preferred compounds of formula I are those in which $R_1$ is methyl or ethyl; $R_2$ is methyl, ethyl, isopropyl or butyl; $R_3$ and $R_4'$, which may be the same or different, are hydrogen, methyl, methoxy, methylthio, methylsulphinyl, methanesulphonate; fluoro, trifluoromethyl, trifluoromethoxy, 2,2,2-trifluoroethyoxy, cyano or phenyl; and $R_5$ is hydrogen.

Especially preferred compounds of formula I are those in which $R_1$ is methyl or ethyl; $R_2$ is methyl; $R_3$ and $R_4$, which may be the same or different, are hydrogen, methyl, methoxy, methylthio, methylsulphinyl, fluoro, chloro, trifluoromethyl, trifluoromethoxy or cyano; and $R_5$ is hydrogen.

In a preferred group of compounds of formula I $R_1$ is methyl or ehtyl; $R_2$ is methyl; $R_3$ is hydrogen, methyl, methoxy, methylthio, methylsulphinyl, fluoro, chloro, trifluoromethyl, trifluoromethoxy or cyano; and $R_4$ and $R_5$ are hydrogen.

Specific compounds of formula I are:
1-methyl-1,4-dihydroquinol-3-yl methanesulphonate;
7-fluoro-1-methuyl-4-oxo-1,4dihydroquinol-3-yl methanesulphonate;
1-methyl-4-oxo-1,4-dihydroquinol-3-yl1-butanesulphonate;
8-fluoro-1 -methyl-4-oxo-1,4-dihydroquinol-3-yl methanesulphonate;
6-fluoro-1-methyl-4-oxo-1,4-dihydroquinol-3-yl methanesulphonate;
1-methoxy-4-oxo-7-(2,2,2-trifluoroethoxy)-1,4-dihydroquinol-3-yl methanesulphonate.
1,7-dimethyl-4-oxo-1,4-dihydroquinol-3-yl methanesulphonate;
1-ethyl-4-oxo-1,4-dihydroquinol-3yl methanesulphonate;
7-methoxy-1-methyl-4-oxo-1,4dihydroquinol-3-yl methanesulphonate;
7-fluoro-1-methyl-4-oxo-1,4dihydroquinol-3-yl ethanesulphonate;
1-methyl-4--oxo-7-trifluoromethyl-1,4-dihydroquinol-3-yl methanesulphonate;
7-cyano-1-methyl-4oxo-1,4-dihydroquinol-3-yl methanesulphonate;
1--methyl-7--methylthio-4-oxo-1,4dihydroquinol-3-yl methanesulphonate;
1-methyl-7-methylsulphinyl-4-oxo-1,4-dihydroquinol-3-yl methanesulphonate;
1-methyl-7-methylsulphonyl-4-oxo-1,4-diyhydroquinol-3-yl methanesulphonate;
7-chloro--1-methyl-4oxo-1,4-dihydroquinol-3yl methanesulphonate;
6,7-difluoro-1-methyl-4-oxo-1,4-dihydroquinol-3-yl methanesulphonate;
6,7dimethyoxyyy-1methyl-4-oxo-1,4-dihydroquinol-3yl methanesulphonate;
1-methyl-4-poxpo-7-trifluoromethoxy,-1,4dihydroquinol-3-yl methanesulphonate;
7-fluoro-1-methyl-4oxo-1,4-dihydroquinol-3yl 2-propanesulphonate;
1-methyl-4-oxo-7-phenyl-1,4-dihydroquinol-3-yl methanesulphonate;
6--chloro-1-methyl-4oxo-1,4-dihydroquinol--3-yl methanesulphonic; and
6-methoxy-1,7-dimethyl-4oxo-1,4dihydroquinol-3-yl methanesulphonate.

A preferred group of compounds of formula I may be represented by formula II

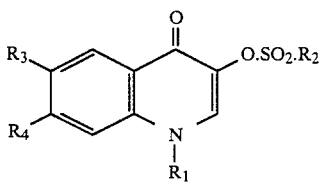

in which $R_1$ is lower alkyl; $R_2$ is lower alkyl; and $R_3$ (in the 6-position) and $R_4$ (in the 7-position), which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo.

Preferred compounds of formula II are those in which $R_1$ is alkyl having 1 to 4 carbon atoms; $R_2$ is alkyl having 1 to 4 carbon atoms; and $R_3$ and $R_4$, which may be the same or different, are hydrogen, alkyl having 1 to 4 carbon atoms, alkoxy having 1 to 4 carbon atoms, alkylthio having to 4 carbon atoms, alkylsulphinyl having 1 to 4 carbon atoms, alkylsulphonyl having 1 to 4 carbon atoms, halo, fluorinated alkyl having 1 to 4 carbon atoms, fluorinated alkoxy having 1 to 4 carbon atoms, cyano, phenyl or phenyl substituted by 1 or 2 groups independently selected from alkyl having 1 to 4 carbon atoms, alkoxy having 1 to 4 carbon atoms and halo.

In one preferred group of compounds of formula II, $R_1$ is methyl or ethyl, $R_2$ is methyl and $R_3$ and $R_4$ are each independently selected from hydrogen, alkyl having 1 to 4 carbon atoms, alkoxy having 1 to 4 carbon atoms and halo.

Preferred compounds of formula II are those in which $R_1$ is methyl or ethyl; $R_2$ is methyl, ethyl, isopropyl or butyl; and one of $R_3$ and $R_4$ is hydrogen and the other is hydrogen, methyl, methoxy, methylthio, methylsulphinyl, methylsulphonyl, fluoro, chloro, trifluoromethyl, trifluoromethoxy, 2,2,2-trifluoroethoxy, cyano or phenyl.

In a further group of preferred compounds of formula II, $R_1$ and $R_2$ are methyl and one of $R_3$ and $R_4$ is hydrogen and the other is hydrogen, methyl, methoxy, methylthio, methylsulphinyl, fluoro, chloro, trifluoromethyl, trifluoromethoxy or cyano.

In one particularly preferred group of compounds of formula II, $R_1$) and $R_2$ are methyl; $R_3$ is hydrogen and $R_4$ is hydrogen, methyl, methoxy, methylthio, fluoro, chloro, trifluoromethyl or trifluoromethoxy. Especially preferred compounds of formula II are 1-methyl-4-oxo-1,4-dihydroquinol-3-yl methanesulphonate, 7-fluoro-1-methyl-4-oxo-1,4-dihydroquinol-3-yl methanesulphonate, and 7-chloro-)-methyl-4-oxo-1,4-dihydroquinol-3-yl methanesulphonate.

In a further particularly preferred group of compounds of formula II, $R_1$ and $R_2$ are methyl; $R_3$ is chloro or fluoro; and $R_4$ is hydrogen. An especially preferred compound is 6-fluoro-1-methyl-4-oxo-1,4-dihydroquinol-3-yl methanesulphonate.

Certain compounds of formula I may exist in more than one crystal form. For example, 1-methyl-4-oxo-1,4-dihydroquinol-3-yl methanesulphonate can exist in at least two crystal forms, each having a characteristic infra-red spectrum. Conversion of a less thermodynamically stable crystal form of 1-methyl-4-oxo-1,4-dihydroquinol-3-yl methanesulphonate to a more thermodynamically stable crystal form may be effected, for example, by recrystallisation with rapid cooling and agitation from a solvent such as industrial methylated spirit or by heating the solid, for example at 160° C. The present invention includes each of the crystal forms of compounds of formula I and mixtures thereof.

It will be appreciated by those skilled in the art that compounds of formula I in which one or more of the substituents $R_1$, $R_2$, $R_3$, $R_4$ and $R_5$ contains a chiral centre may exist as two or more stereochemical isomers. When the compounds of formula I contain one chiral centre, the compounds may exist in two enantiomeric forms and the present invention includes both enantiomeric forms and mixtures thereof. When the compounds of formula I contain more than one chiral centre, the compounds may exist in diastereoisomeric forms. The present invention includes each of these diastereoisomeric forms and mixtures thereof.

Compounds of formula I may exist in the form of solvates, for example hydrates, and the present invention includes such forms and mixtures thereof.

The present invention also provides pharmaceutical compositions which comprise a compound of formula I as hereinbefore defined together with a pharmaceutically acceptable carrier. Specific compounds which may be incorporated in the compositions of this invention are the novel compounds disclosed above.

In therapeutic use a compound of formula I may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention suitably contain 0.1–90% by weight of a compound of formula I. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art.

Tablets may be prepared by mixing the compound of formula I with an inert diluent, such as calcium phosphate, in the presence of disintegrating agents, for example maize starch, and lubricating agents, for example magnesium stearate, and tableting the mixture by known methods. Such tablets may if desired be provided with enteric coatings by known methods, for example by the use of cellulose acetate phthalate. Similarly capsules, for example hard or soft gelatin capsules containing the compound of formula I with or without added excipients, may be prepared by conventional means and, if desired, provided with enteric coatings in a known manner. Enteric coated compositions of the invention may be advantageous, depending on the nature of the compound of formula I. The tablets and capsules may conveniently each contain 1–500 mg of the compound of formula I. Other compositions for oral administration include, for example aqueous suspensions containing the compound of formula I in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the compound of formula I is dispersed so that it is held in contact with the skin in order to administer the compound of formula I transdermally. Alternatively the compound of formula I may be dispersed in a cream or ointment base.

In some formulations it may be beneficial to use the compounds of the present invention in the form of particles of very small size, for example as obtained by fluid energy milling.

In the compositions of the present invention the compound of formula I may, if desired, be associated with other compatible pharmacologically active ingredients, for example a β-blocker such as propranolol, oxprenolol, atenolol, nadolol or timolol, or a diuretic such as bendrofluazide.

The therapeutic activity of compounds of formula I has been demonstrated by means of tests on standard laboratory animals. Such tests include, for example, the oral administration of the compounds to a strain of spontaneously hypertensive rat. Thus, compounds of formula I are useful for reducing blood pressure in hypertensive mammals. A suitable dose for enteral administration to mammals, including humans, is generally within the range 0.0–25 mg/kg/day, more usually 0.2–10 mg/kg/day given in single or divided doses. For parenteral administration, a suitable dose is generally within the range 0.001–2.5 mg/kg/day, especially 0.005–1 mg/kg/day. Oral administration is preferred.

Compounds of formula I are vasodilators with an action on both arteriolar and venous vascular beds. Accordingly, compounds of formula I are indicated for use in the treatment of ischaemic heart disease and heart failure in mammals, including humans. Suitable dosages are as hereinbefore stated.

The compounds of formula I may be prepared by reaction of a compound of formula III

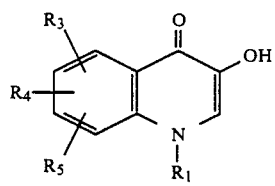

III with a lower alkanesulphonylating agent, for example a sulphonyl halide of formula $R_2.SO_2.Hal$ in which Hal is halo, preferably chloro, (for example methanesulphonyl chloride), in the presence of a base, for example sodium hydroxide or triethylamine.

Compounds of formula I may also be prepared by alkylation of a compound of formula IV

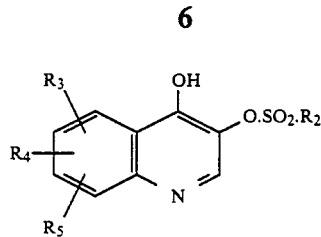

IV with an alkylating agent of formula $(R_1)_2SO_4$ or an alkylating agent of formula $R_1Y$ where Y is a leaving group, for example halo, preferably iodo. The reaction may preferably be carried out in the presence of a base, for example potassium carbonate. Alternatively, compounds of formula I may be prepared by cyclisation of a compound of formula V

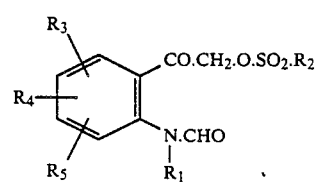

V for example by use of a base such as 1,8-diazabicyclo-[5.4.0]undec-7-ene in anhydrous conditions, for example in the presence of molecular sieves.

Compounds of formula I in which at least one of $R_3$, $R_4$ and $R_5$ represents a group of formula $—S(O)_nR$ in which R is lower alkyl and n is 1 or 2 may be prepared by oxidation of a corresponding compound of formula I in which n is 0 or 1, using for example, a peroxycarboxylic acid such as m-chloroperoxybenzoic acid as the oxidising agent.

Compounds of formula III may be prepared from a compound of formula VI

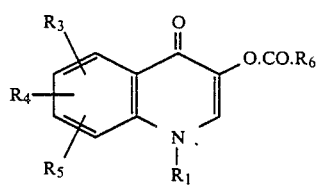

VI in which $R_6$ is lower alkyl or aryl, by deacylation, for example debenzoylation of a compound of formula VI in which $R_6$ is phenyl, with a suitable nucleophilic reagent, for example piperidine.

Compounds of formula III may also be prepared by the reaction of a compound of formula VII

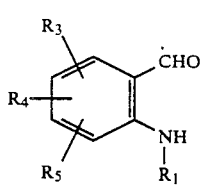

VII with, for example, glyoxal, as the sodium bisulphite addition compound, in a similar manner to that described by D J Evans and F W Eastwood, Aust.J.-Chem., 27, 537, (1974) for the reaction of 2-(methylamino)-benzaldehyde to give the known compound of formula III in which $R_1$ is methyl and $R_3$, $R_4$ and $R_5$ are all hydrogen. Novel compounds of formula VII may be prepared by processes analogous to those described for the preparation of the known compound of formula VII, 2-(methylamino)benzaldehyde.

Compounds of formula III in which R4 in the 7-position is lower alkoxy, lower alkylthio, lower alkylsulphonyl, halogenated lower alkoxy or cyano may also be prepared from a compound of formula VIII

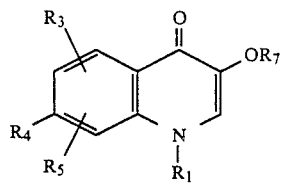

in which $R_7$ is a protecting group, such as lower alkenyl, for example allyl, by deprotection, for example when $R_7$ is allyl by reaction with Wilkinson's catalyst, tris(triphenylphosphine)rhodium chloride.

Compounds of formula IV may be prepared by reaction of a compound of formula IX

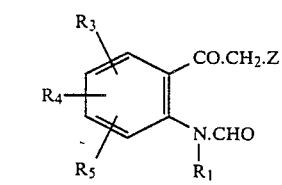

with a lower alkanesulphonylating agent, for example an alkanesulphonic anhydride of formula $(R_2SO_2)_2O$, such as methanesulphonic anhydride, in the presence of a base, for example potassium carbonate.

Compounds of formula V may be prepared by reacting a compound of formula X

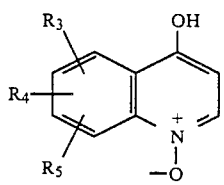

in which Z is a leaving group, for example halo, preferably chloro or bromo, with a lower alkanesulphonating agent, for example silver methanesulphonate.

Compounds of formula VI may be prepared by cyclisation of a compound of formula XI

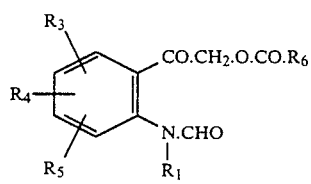

for example in the presence of a base with little or no nucleophilic character such as potassium carbonate.

Compounds of formula VIII may be prepared from a compound of formula XII

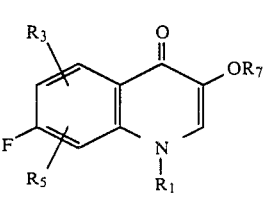

by reaction with an appropriate nucleophilic reagent, for example, compounds of formula VIII in which R4 is methoxy or 2,2,2-trifluoroethoxy may be prepared from a compound of formula XII by reaction with sodium methoxide or sodium 2,2,2-trifluoroethoxide respectively.

Compounds of formula IX may be prepared by hydrolysis of a compound of formula XIII

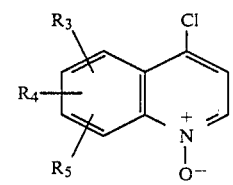

by reaction with a base, for example sodium hydroxide in ethanol.

Compounds of formula X may be prepared by formylation of a compound of formula XIV

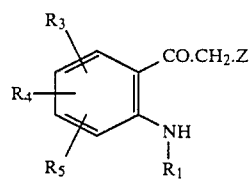

for example by reaction with acetic formic anhydride.

Compounds of formula X in which Z is halo may also be prepared by halogenation of a compound of formula XV

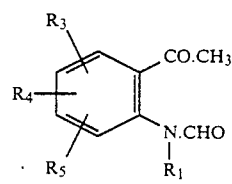

with a halogenating agent, for example by reaction with sulphuryl chloride to give compounds of formula X in which Z is chloro.

Compounds of formula XI may be prepared from a compound of formula X by reaction with a carboxylic acid or derivative thereof, for example sodium benzoate, optionally in the presence of a base, for example triethylamine.

Compounds of formula XI may also be prepared by formylation of a compound of formula XVI

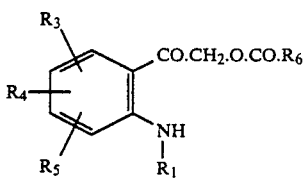
XVI for example by reaction with acetic formic anhydride.

Compounds of formula XII may be prepared from a compound of formula III in which R₄ is fluoro in the 7-position. Thus, the hydroxyl group of a compound of formula III may be protected for example by an allyl group by reaction of a compound of formula III with sodium hydride followed by allyl bromide.

Compounds of formula XIII may be prepared from a compound of formula XVII

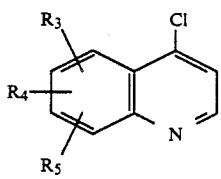
XVII by reaction with a suitable oxidising agent, for example m-chloroperoxybenzoic acid.

Compounds of formula XIV in which Z is halo may be prepared by orthohaloacetylation of a compound of formula XVIII

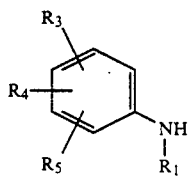
XVIII for example by reaction with chloroacetonitrile followed by hydrolysis to give compounds of formula XIV in which Z is chloro.

Compounds of formula XV may be prepared by formylation of a compound of formula XIX

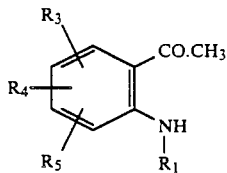
XIX for example by reaction with acetic formic anhydride.

Compounds of formula XVI may be prepared by alkylation of a compound of formula XX

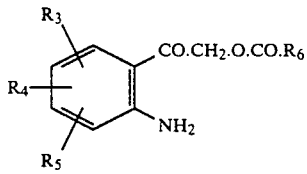
XX with an alkylating agent of formula $(R_1)_2SO_4$ or an alkylating agent of formula $R_1Y$ where Y is a leaving group, for example halo, preferably iodo. The reaction is carried out in the presence of a base, for example potassium carbonate.

Compounds of formula XVIII may be prepared by hydrolysis of a compound of formula XXI

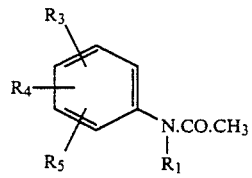
XXI for example by reaction with sodium hydroxide in aqueous industrial methylated spirit.

Compounds of formula XIX may be prepared by alkylamination of a compound of formula XXII

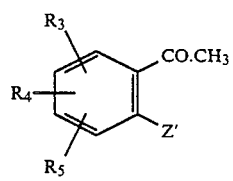
XXII in which Z' is a leaving group, preferably chloro or fluoro, for example by reaction with a primary alkylamine of formula $R_1NH_2$, such as methylamine in the presence of a metal catalyst, for example copper. It will be appreciated by those skilled in the art that the keto group in compounds of formula XIX and XXII may react with the alkylamine and hydrolysis may be required to give the desired compounds of formula XIX.

Compounds of formula XIX may also be prepared by alkylation of a compound of formula XXIII

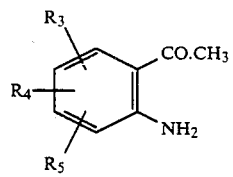
XXIII with an alkylating agent of formula $(R_1)_2SO_4$ or an alkylating agent of formula $R_1Y$ where Y is a leaving group, for example halo, preferably iodo. The reaction is carried out in the presence of a base, for example potassium carbonate.

Alternatively, compounds of formula XIX may be prepared by reduction of a compound of formula XXIV

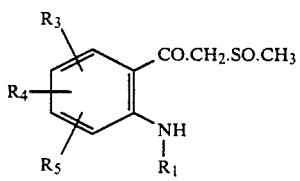
XXIV for example with powdered zinc in the presence of acetic acid.

Compounds of formula XX may be prepared by reduction of a compound of formula XXV

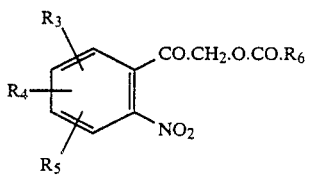

XXV for example with finely divided iron in the presence of aqueous ammonium chloride.

Compounds of formula XXI may be prepared by alkylation of a compound of formula XXVI

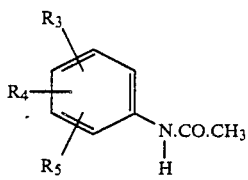

XXVI with an alkylating agent of formula $(R_1)_2SO_4$ or an alkylating agent of formula $R_1Y$ where Y is a leaving group, for example halo, preferably iodo. The reaction is carried out in the presence of a base, for example sodium hydride.

Compounds of formula XXV may be prepared from a compound of formula XXVII

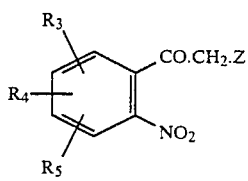

XXVII in which Z is a leaving group, for example halo, preferably chloro or bromo, by reaction with a carboxylic acid or derivative thereof, for example sodium benzoate, optionally in the presence of a base, for example triethylamine.

Some of the compounds of formulae XVII, XVIII, XXII, XXIII, XXIV, XXVI and XXVII are known but it will be apparent to those skilled in the art that the novel compounds may be prepared in a similar manner to the preparation of the known compounds of said formulae.

Many of the intermediates mentioned hereinbefore are believed to be novel compounds and such novel intermediates form a further aspect of the present invention.

Particularly valuable intermediates of the processes of the present invention are the compounds of formulae III, IV, V, VI, VII, VIII, X, XI and XII.

The novel intermediate compounds of formula IV

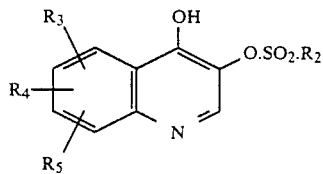

IV in which $R_2$ is lower alkyl and $R_3$, $R_4$ and $R_5$, which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo, form a particularly preferred aspect of the present invention.

A further preferred group of intermediates are the novel N-formal compounds of formula XXVIII

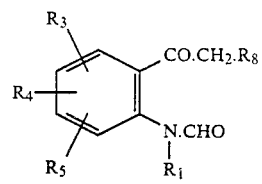

XXVIII in which $R_1$ is lower alkyl; $R_3$, $R_4$ and $R_5$, which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo; and $R_8$ is halo, lower alkanesulphonyloxy or a group of formula —O.-CO.$R_6$ in which $R_6$ is lower alkyl or aryl; with the proviso that when $R_3$ and $R_5$ are hydrogen, $R_4$ is fluoro or chloro in the position para to the group —CO.CH2.$R_8$ and $R_8$ is halo, $R_1$ contains more than one carbon atom.

Compounds of formula XXVIII in which $R_8$ is lower alkanesulphonyloxy are especially preferred intermediates and have antihypertensive activity.

A still further group of preferred intermediates are the novel quinolones of formula XXIX

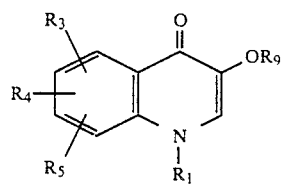

XXIX in which $R_1$ is lower alkyl; $R_3$, $R_4$ and $R_5$, which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by or 2 groups independently selected from lower alkyl, lower alkoxy and halo; and $R_9$ is hydrogen, a group of formula —CO.$R_6$ in which $R_6$ is lower alkyl or aryl or, when $R_3$ and $R_5$ are hydrogen and $R_4$ is fluoro, lower alkoxy, lower alkylthio, lower alkylsulphonyl, halogenated lower alkoxy or cyano in the 7-position, lower alkenyl; with the proviso that when $R_3$, $R_4$, $R_5$ and $R_9$ are all hydrogen, $R_1$ contains more than one carbon atom.

Compounds of formula XXIX in which $R_9$ is hydrogen are especially preferred intermediates.

The particularly preferred group of compounds of formula II may be prepared using appropriate methods disclosed hereinbefore for preparing compounds of formula I.

The therapeutic activity of compounds of formula I in Table 1 has been demonstrated by the following test which involves the oral administration of the compounds to a strain of spontaneously hypertensive rat. This test was carried out in the following way:

Test

Female rats, weight range 180-240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. The degree of blood pressure reduction sufficient to achieve a significance level of $p<0.01$ compared to controls was after correction for control changes at appropriate time intervals. Thus the activity threshold was considered to be 9% after correction.

Threshold antihypertensive doses of compounds of formula I were determined in the following way. Compounds were tested initially at a particular dose level, for example 90 mg/kg. If the compound was considered sufficiently active (giving a reduction of blood pressure equal to or greater than 16% after correction) it was retested at a lower dose level, for example 30 mg/kg. By testing at successively lower dose levels, a threshold antihypertensive dose (dose giving a reduction of blood pressure of between 9 and 16% after correction) was determined. Compounds inactive at a particular dose level and giving a reduction of blood pressure equal to or greater than 16% after correction at the next highest dose level were designated as having a threshold antihypertensive dose within the range covered by the two dose levels.

The final products of Examples 1 to 29 were active in this test at a dose level of 90 mg/kg or less and the actual results obtained to date are shown in Table 1 below. Where a compound is active at a particular dose level but has not yet been tested at lower dose levels a threshold antihypertensive dose of less than or equal to ($\leq$) the dose level tested is given.

TABLE 1

| Final Product of Example | Threshold antihypertensive dose (mg/kg) |
|---|---|
| 1 (Also 2,4,18,19, 20,28 and 29) | 0.3 |
| 3 | 1 |
| 5 | 90 |
| 6 | 10 to 30 |
| 7 (Also 27) | 1 to 3 |
| 8 | 90 |
| 9 | 10 |
| 10 | 10 to 30 |
| 11 | 10 |
| 12 | 90 |
| 13 | 10 |
| 14 | $\leq$30 |
| 15 | 10 |
| 16 | 30 |

TABLE 1-continued

| Final Product of Example | Threshold antihypertensive dose (mg/kg) |
|---|---|
| 17 | 90 |
| 21 | 0.1 |
| 22 | 3 to 10 |
| 23 | 3 to 10 |
| 24 | 3 |
| 25 | 90 |
| 26 | 90 |
| 27 | $\leq$90 |

The invention is illustrated by the following non-limitative Examples in which compositions of mixed solvents are given by volume. Novel compounds were characterised by one or more of the following: elemental analysis, nuclear magnetic resonance, infra-red and mass spectroscopy. Temperatures are given in degrees Celsius.

Flash chromatography was performed according to the method of Still et al., J. Org. Chem., 43 2923-5 (1978).

When used as a dispersion in mineral oil, sodium hydride was washed with petroleum ether (b.p. 40°-60°) prior to use. The weight quoted in the Examples refers to the weight of disperson used prior to washing.

EXAMPLE 1

(a) Potassium carbonate (19 g) was added to a stirred suspension of benzoic acid (34 g) in water (600 ml) and the mixture was warmed gently on a steam bath. After 15 minutes, 2-bromo-2'-nitroacetophenone (68 g) and industrial methylated spirit (1 l) were added. The resultant mixture was heated under reflux for 2 hours, stirred without external heating for 1 0 minutes and then rapidly cooled to 0°-5° in an ice/salt bath with agitation. The mixture was kept at this temperature for 90 minutes and the product was collected by filtration and washed with water to give the novel compound 2-(2-nitrophenyl)-2-oxoethyl benzoate, m.p. 77-80°.

(b) A mixture of 2-(2-nitrophenyl)-2-oxoethyl benzoate (50 g) and ammonium chloride (1 0.75 g) in water (800 ml) was stirred at 90° for 20 minutes. Iron powder (80 g) was added gradually over a period of 20 minutes. The mixture was stirred at 95° for a further 3 hours and filtered hot through diatomaceous earth (sold under the trade name CELITE). The filter bed was washed with hot (80°) water (100 ml) and then separately with hot (60°) ethyl acetate (5×300 ml). The aqueous filtrate and aqueous washing were combined and extracted with ethyl acetate (4×400 ml) and the extracts combined with the ethyl acetate washings from above, which had been washed with aqueous sodium chloride (6M, 200 ml). The combined ethyl acetate extracts were dried over sodium sulphate and evaporated to give the novel compound 2-(2-aminophenyl)-2-oxoethyl benzoate, m.p. 125°.

(c) Iodomethane (55.8 ml) was added to a stirred suspension of 2-(2-aminophenyl)-2-oxoethyl benzoate (109 g) and potassium carbonate (1 )8 g) in dry dimethylformamide (400 ml) at ambient temperature. The mixture was stirred at this temperature for 21hours and then at 40° for 5 hours. The solvent was removed under reduced pressure at 60°, water (100 ml) was added and the mixture extracted with dichloromethane (3×200 ml). The combined extracts were dried over sodium sulphate and the solvent was removed by evaporation to leave a dark oil. The oil was purified by flash chromatography on a silica gel column eluted with dichloromethane to give the novel compound 2-[2(methylamino)phenyl]-2-oxoethyl benzoate, m.p. 85°–87°.

(d) A mixture of acetic anhydride (67 ml) and formic acid (98%, 49 ml) was stirred at 55° for 2 hours and then cooled in an ice/water bath to 20°. 2-[2(Methylamino)phenyl]-2-oxoethyl benzoate (79.5 g) was added in portions whilst maintaining the temperature below 30° and the mixture was stirred for 5 hours. The solvent was removed under reduced pressure at 60° and the residue was stirred with petroleum ether (b.p. 40°–60°, 500 ml) for 2 hours. The resulting solid was collected by filtration and washed with petroleum ether (b.p. 40°–60°, 200 ml) to give the novel compound 2-[2-(N-methylformamido)phenyl]-2-oxoethyl benzoate, m.p. 100°–102°.

(e) A mixture of 2-[2-(N-methylformamido)phenyl]-2oxoethyl benzoate (84 g), potassium carbonate (39.2 g) and dry dimethylformamide (1100 ml) was stirred at 50 to 60° for 4 hours. The solvent was removed under reduced pressure at 60° and the residue was triturated with water (700 ml). The resultant solid was collected by filtration and washed with water (4×250 ml) followed by diethyl ether (250 ml) to give the novel compound 1-methyl-4-oxo-1,4-dihydroquinol-3-yl benzoate, m.p.2)5–21 7°.

(f) A mixture of 1-methyl-4-oxo-1,4-dihydroquinol-3-yl benzoate (45 g), piperidine (16.9 ml) and dichloromethane (700 ml) was stirred for 3 days at ambient temperature under nitrogen. A further portion of piperidine (3 ml) was added and the stirring continued for 1 day. The solvent was removed by distillation at 50° and the residue was triturated with diethyl ether (300 ml). The resultant solid was collected by filtration and washed with diethyl ether (2×100 ml) to give 3-hydroxy-1-methyl-4-quinolone, m.p. 243°–246°.

(g) 3-Hydroxy-1-methyl-4-quinolone (30 g) was dissolved in a solution of sodium hydroxide (8 g) in water (440 ml). Activated carbon (3 g) was added and the mixture stirred at 40° for 15 minutes. The mixture was filtered and the filtrate cooled in an ice/salt bath at 0 to 5° under nitrogen. Methanesulphonyl chloride (1 5.5 ml) was added dropwise over 30 minutes and the mixture then stirred at 0 to 5° for 30 minutes. Aqueous sodium hydroxide (5M, 40 ml) was added and the mixture stirred at 0 to 5° for a further 90 minutes. The resultant solid was collected by filtration and washed with water (2×50 ml) to yield crude product. The filtrate was treated with further methanesulphonyl chloride (15.5 ml) in a similar manner to that described above to give a second crop of crude product. The two crops of crude product were combined and crystallised from industrial methylated spirit (2 1) to give the novel compound 1-methyl-4-oxo-1,4-dihydroquinol-3-yl methanesulphonate, m.p. 208°–209°.

EXAMPLE 2

(a) A mixture of 2'-chloroacetophenone (182 g), industrial methylated spirit (290 ml), methylamine (33% w/w solution in industrial methylated spirit, 3)3 ml) and copper powder (2.8 g) was stirred in a sealed pressure vessel for 5 hours at 90°. The reaction vessel was allowed to cool to ambient temperature and the mixture washed out of the vessel with industrial methylated spirit (2×100 ml). The combined reaction mixture and washings were stirred at 50°, a solution of sodium sulphide nonahydrate (24 g) in water (100 ml) was added over a period of 10 minutes, and stirring and heating were continued for a further 15 minutes. The mixture was filtered through diatomaceous earth (sold under the trade name CELITE) and the filter bed washed with industrial methylated spirit (100 ml). The filtrate was evaporated to give an oil which was stirred with hydrochloric acid (5M, 800 ml) for 1 hour. The resultant mixture was extracted with dichloromethane (600 ml, then 2×300 ml) and the combined extracts were washed with water (500 ml), dried over magnesium sulphate and evaporated to give an oil which was then distilled. The fraction distilling at 100°–110° and 5 mmHg was collected to give 2'-(methylamino)acetophenone, m.p. 36°–38°. The aqueous acid phase from above was basified by the addition of aqueous sodium hydroxide (specific gravity 1.5, 230 ml). The resultant mixture was extracted with dichloromethane (500 ml, then 250 ml) and the combined extracts were washed with water (300 ml), dried over magnesium sulphate and evaporated to give an oil. Trituration with petroleum ether (b.p. 40°–60°, 200 ml) gave a second crop of 2'-(methylamino)acetophenone, m.p. 36°–38°.

(b) A mixture of acetic anhydride (147.2 ml) and formic acid (98%, 100.3 ml) was stirred at 50°–60° for 110 minutes and then cooled to ambient temperature. 2'-(Methylamino)acetophenone (100 g) was added in portions over a period of 30 minutes whilst maintaining the temperature below 30°. The mixture was stirred at ambient temperature for 90 minutes and then cooled to 0°. Water (512 ml) was added over a period of 20 minutes, followed by aqueous sodium hydroxide (specific gravity 1.5, 288 ml) added over a period of 85 minutes whilst maintaining the temperature below 10°. The reaction mixture was transferred to a separating funnel, dichloromethane (200 ml) was added, followed by hydrochloric acid (2M) to pH 9, and the dichloromethane layer separated. The aqueous layer was further extracted with dichloromethane (2×200 ml). The combined dichloromethane extracts were washed with aqueous sodium chloride (6M, 200 ml) and then dried over magnesium sulphate to give a solution of 2'-acetyl-N-methylformanilide.

(c) A solution of sulphuryl chloride (119 ml) in dichloromethane (168 ml) was added dropwise to the o solution of 2'-acetyl-N-methylformanilide at 0° under a nitrogen atmosphere. The mixture was stirred for 2 hours at 0° and then cold (5°) water (488 ml) was added dropwise over a period of 1 hour. The dichloromethane layer was separated and dried over magnesium sulphate to give a solution of 2'-(2-chloroacetyl)-N-methylformanilide.

(d) Triethylamine (362.8 ml) was added to a stirred mixture of benzoic acid (239.1 g) and dichloromethane (1120 ml) at 0° and the resultant solution was added dropwise over a period of 1 hour to the solution of 2'-(2-chloroacetyl)-N-methylformanilide under nitrogen whilst maintaining the temperature below 5°. The resulting solution was stirred overnight at ambient temperature, washed with water (2×1250 ml), dried over magnesium sulphate and the solvent removed by distillation at 50° to give a solid residue. Trituration with petroleum ether (b.p. 60°–80°, 1 1) gave the novel compound 2-[2-(N-methylformamido)phenyl]-2-oxoethyl benzoate, m.p. 100°–102°.

(e) The 2-[2-(N-methylformamido)phenyl]-2-oxoethyl benzoate can be similarly treated as previously disclosed in Example 1(e), 1(f) and 1(g) to give 1-methyl-4-oxo-1,4-dihydroquinol-3-yl methanesulphonate, m.p. 208°–209°.

EXAMPLE 3

(a) A mixture of 4'-fluoro-2'-chloroacetophenone (40 g), methylamine (33% w/w solution in industrial methylated spirit, 60 ml), industrial methylated spirit (40 ml) and copper powder (0.5 g) was stirred at 80° in a sealed pressure vessel for 3 hours. After cooling to ambient temperature, the reaction mixture was transferred to a conical flask. The reaction vessel was washed out with industrial methylated spirit (2×30 ml) and the washings added to the reaction mixture. Sodium sulphide nonahydrate (2.3 g) in water (23 ml) was added and the mixture heated at 50° for 10 minutes. The mixture was filtered through diatomaceous earth (sold under the trade name CELITE). Solvent was removed from the filtrate under reduced pressure at 40° and hydrochloric acid (5M, 160 ml) was added to the residue. The mixture was stirred for approximately 2 hours and then extracted with dichloromethane (100 ml, then 2×60 ml). The combined extracts were dried over magnesium sulphate and evaporated to give the novel compound 4'-fluoro-2'-(methylamino)acetophenone as an oil which solidified on storing at ambient temperature.

(b) A mixture of acetic anhydride (26.5 ml) and formic acid (98%, 17.4 ml) was stirred at 50°–60° for 110 minutes and then cooled to ambient temperature. 4'-Fluoro-2'-(methylamino)acetophenone (19.9 g) was added and the mixture stirred overnight at ambient temperature. Water (90 ml) was added and the mixture stirred in an ice/salt bath. Aqueous sodium hydroxide (specific gravity 1.5, 50 ml) was added dropwise over a period of 30 minutes whilst maintaining the temperature below 30°. The mixture was extracted with dichloromethane (3×50 ml) and the combined extracts were dried over magnesium sulphate to give a solution of 2'-acetyl-5'-fluoro-N-methylformanilide.

(c) A solution of sulphuryl chloride (20.6 ml) in dichloromethane (30 ml) was added dropwise over a period of 45 minutes to the solution of 2'-acetyl-5'-fluoro-N-methylformanilide whilst maintaining the temperature below 2° with ice/water cooling under a nitrogen atmosphere. The mixture was stirred for 3 hours maintaining the temperature below 2°. Water (80 ml) was added dropwise over 15 minutes maintaining the temperature below 10°. The dichloromethane layer was separated and dried over magnesium sulphate to give a solution of 2'-(2-chloroacetyl)-5'-fluoro-N-methylformanilide.

(d) Benzoic acid (42.7 g) and triethylamine (64.8 ml) were dissolved in dichloromethane (250 ml) at 0° and this solution was added to the dichloromethane solution of 2'-(2-chloroacetyl)-5'-fluoro-N-methylformanilide over a period of hour whilst maintaining the temperature below 5° with ice/water bath cooling. After stirring for 1 hour at 5°, the mixture was heated under reflux under nitrogen for 16 hours. Further triethylamine (16 ml) was added and the mixture heated under reflux for a further 16 hours. The mixture was allowed to cool to ambient temperature, washed with water (2×250 ml) and dried over magnesium sulphate. Evaporation of the solvent gave the novel compound 2-[4-fluoro-2-(N-methylformamido)phenyl]-2-oxoethyl benzoate, m.p. 93°–95°.

(e) A mixture of 2-[4-fluoro-2-(N-methylformamido)phenyl]-2-oxoethyl benzoate (28 g), potassium carbonate (13.1 g) and dry dimethylformamide (360 ml) was stirred at 60° for 4 hours under nitrogen. The solvent was removed under reduced pressure at 60°. The resultant residue was triturated with water (3×300 ml), then diethyl ether (2×150 ml) to give the novel compound 7-fluoro-1-methyl-4-oxo-1,4-dihydroquinol-3-yl benzoate, m.p. 214°–215°.

(f) A mixture of 7-fluoro-1-methyl-4-oxo-1,4-dihydroquinol-3-yl benzoate (1 0 g), piperidine (3.7 ml) and dichloromethane (200 ml) was stirred at ambient temperature for 2 days under nitrogen. The solvent was removed by distillation at 50°. The resultant solid was triturated with diethyl ether 100 ml), collected and washed with diethyl ether (2×100 ml) to give the novel compound 7-fluoro-3-hydroxy-1-methyl-4-quinolone, m.p. 283°–285°.

(g) 7-Fluoro-3-hydroxy-1-methyl-4-quinolone (4.5 g) was added to a solution of sodium hydroxide (12 g) in water (56 ml) and the mixture stirred at 0 to 5° with ice/water cooling. Methanesulphonyl chloride (4 ml) was added over a period of 1 5 minutes followed by aqueous sodium hydroxide (5M, 3 ml). The resultant solid was collected by filtration, washed with water (2×20 ml), and crystallised from industrial methylated spirit (220 ml) to give the novel compound 7-fluoro-]-methyl-4-oxo-1,4-dihydroquinol-3-yl methanesulphonate, m.p. 212°–213°.

EXAMPLE 4

(a) A mixture of 4-hydroxyquinoline-1-oxide (1 g), methanesulphonic anhydride (2 g) and potassium carbonate (2 g) in dichloromethane (20 ml) was stirred at 0° for 4 hours. Water (20 ml) was added to the mixture and the dichloromethane layer separated. The aqueous layer was extracted with dichloromethane (2×60 ml). The combined dichloromethane layer and extracts were dried over magnesium sulphate and evaporated to give a gum which was purified by flash chromatography on a silica gel column eluted with dichloromethane:methanol (19:1) to give the novel compound 4-hydroxyquinol-3-yl methanesulphonate, m.p. 224°.

(b) A mixture of 4-hydroxyquinol-3-yl methanesulphonate (0.48 g) and potassium carbonate (0.28 g) in dry dimethylformamide (20 ml) was stirred for 2 hours at ambient temperature. Methyl iodide (0.15 ml) was then added and the stirring at ambient temperature continued overnight. The solvent was removed under reduced pressure and the residue was triturated with water (10 ml). The resultant mixture was extracted extracts were evaporated to dryness. The residue was purified by flash chromatography on a silica gel column eluted with dichloromethane:methanol (39:1) followed by crystallisation from industrial methylated spirit (10 ml) to give the novel compound ]-methyl-4-oxo-1,4-dihydroquinol-3-yl methanesulphonate, m.p. 206°–208°.

EXAMPLE 5

3-Hydroxy-1-methyl-4-quinolone (3 g) was suspended in dichloromethane (200 ml), triethylamine (5.6 ml) was added to the suspension and the mixture was stirred at ambient temperature for hour. 1-Butanesulphonyl chloride (2.6 ml) was added to the suspension, the mixture stirred for 90 minutes and then left to stand overnight. The resultant mixture was washed with water (400 ml), aqueous sodium hydroxide (1M, 400 ml) and then further water (3×300 ml). The dichloromethane layer was dried over magnesium sulphate and evaporated to give a solid which was crystallised from methanol (100 ml) to give the novel compound 1-methyl-4- oxo-1,4-dihydroquinol-3-yl 1-butanesulphonate, m.p. 143°–144°.

EXAMPLE 6

(a) A mixture of 2′,3′-difluoroacetophenone (30 g), methylamine (33% w/w solution in industrial methylated spirit, 46.5 ml), industrial methylated spirit (20 ml) and copper powder (1 g) was stirred in a sealed pressure vessel overnight at 100°. The reaction mixture was allowed to cool to ambient temperature and the mixture washed out of the vessel with industrial methylated spirit (2×30 ml). A solution of sodium sulphide nonahydrate (3.7 g) in water (39 ml) was added and the mixture heated at 50° for 15 minutes. The mixture was filtered through diatomaceous earth (sold under the trade name CELITE) and the filter bed washed with industrial methylated spirit (50 ml). The combined filtrate and washing were evaporated to give an oil which was stirred with hydrochloric acid (5M, 120 ml) for 90 minutes. The mixture was neutralised with aqueous sodium hydroxide (5M, 120 ml) and then extracted with dichloromethane (2×150 ml, then 100 ml). The combined extracts were washed with aqueous sodium chloride (6M, 50 ml), dried over magnesium sulphate and evaporated to dryness. The residue was purified by flash chromatography on a silica gel column eluted with dichloromethane:methanol (19:1) to give the novel compound 3′-fluoro-2′-(methylamino)acetophenone, m.p. 26°–28°.

(b) A mixture of acetic anhydride (27 ml) and formic acid (18.4 ml) was stirred at 50° for 135 minutes and then cooled to ambient temperature. 3′-Fluoro-2′ (methylamino)acetophenone (20.48 g) was then added and the solution stirred overnight. Excess acetic formic anhydride was removed under reduced pressure at 30° and the residue then cooled to 5°. Water (92 ml) followed by aqueous sodium hydroxide (specific gravity 1.5) were then added dropwise to pH 7 whilst maintaining the temperature below 5°. The mixture was extracted with dichloromethane (3×35 ml) and the combined extracts were washed with saturated aqueous sodium carbonate (50 ml) then aqueous sodium chloride (6M, 50 ml) and dried over magnesium sulphate to give a solution of 2′-acetyl-6′-fluoro-N-methylformanilide.

(c) A solution of sulphuryl chloride (11.9 ml) in dichloromethane (200 ml) was added dropwise to the solution of 2′-acetyl-6′-fluoro-N-methylformanilide at 0° under a nitrogen atmosphere. The reaction mixture was stirred at 0° for 3.25 hours. Water (100 ml) was added dropwise and the mixture stirred for 30 minutes. The dichloromethane layer was separated, washed with water (160 ml) and dried over magnesium sulphate before removing the solvent under reduced pressure at ambient temperature. The residue was added to a mixture of benzoic acid (22.6 g), potassium carbonate (42.5 g), 25 molecular sieves (4A°, 50 g) and dry dimethylformamide (200 ml) and the resultant mixture stirred at ambient temperature for 3 hours and then at 60° for 2 hours. Further dimethylformamide (600 ml) and potassium carbonate (17 g) were added and the mixture was heated at 60° overnight. The mixture was cooled, filtered and the solvent removed from the filtrate under reduced pressure at 60°. The residue was triturated with water (400 ml) and then with diethyl ether (400 ml). The resultant solid was crystallised from industrial methylated spirit (200 ml) to give the novel compound 8-fluoro-1-methyl-4-oxo-1,4-dihydroquinol-3-yl benzoate, m.p. 179°–181°.

(d) A mixture of 8-fluoro-1-methyl-4-oxo-1,4-dihydro-quinol-3-yl benzoate (10 g), piperidine (3.18 g) and dichloromethane (200 ml) was stirred for 24 hours, a further portion of piperidine (1.7 ml) was added and the stirring continued for a further 24 hours. The solvent was removed by distillation and the residue was triturated with diethyl ether (300 ml). The resultant solid was extracted with aqueous sodium hydroxide (0.1 M, 100 ml) and the extract was neutralised with hydrochloric acid (5M, 2 ml). The resultant precipitate was collected by filtration to give the novel compound 8-fluoro-3-hydroxy-1-methyl-4-quinolone, m.p. 248°.

(e) Methanesulphonyl chloride (1.1 g) d to a solution of 8-fluoro-3-hydroxy-1-methyl-4-quinolone (1.83 g) and sodium hydroxide (0.6 g) in water (15 ml) and the resultant mixture stirred at 0 to 5° for 3 hours with the pH being adjusted to 9 after 20 minutes using aqueous sodium hydroxide (5M, 2 ml). Further methanesulphonyl chloride (1.1 g) was then added and the mixture stirred for 105 minutes whilst maintaining the pH at 9 by the addition of aqueous sodium hydroxide (5M, 2ml). The resultant solid was collected by filtration, washed with water (20 ml) and crystallised from industrial methylated spirit (100 ml) to give the novel compound 8-fluoro-1-methyl-4-oxo-1,4-dihydroquinol-3-yl methanesulphonate, m.p. 207°–209°.

EXAMPLE 7

(a) A mixture of 2′,5′-difluoroacetophenone (20 g), methylamine (33% w/w solution in industrial methylated spirit, 31ml), industrial methylated spirit (30 ml) and copper powder (0.2 g) was heated at 80° in a sealed pressure vessel for 24 hours. The reaction mixture was allowed to cool to ambient temperature and the mixture washed out of the vessel with industrial methylated spirit (2×30 ml). A solution of sodium sulphide nonahydrate (1 g) in water (10 ml) was added to the combined reaction mixture and washings and the mixture heated to 50° for 15 minutes. The mixture was filtered through diatomaceous earth (sold under the trade name CELITE) and the filter bed washed with industrial methylated spirit (50 ml). The combined filtrate and washings were evaporated to give an oil which was stirred with hydrochloric acid (5M, 80 ml) overnight. The mixture was adjusted to pH 8–9 using aqueous sodium hydroxide (specific gravity 1.5) and then extracted with dichloromethane (3×100 ml). The combined extracts were dried over magnesium sulphate and the solvent removed by distillation. The residue was extracted with diethyl ether (100 ml), the extract treated with activated charcoal (5 g) and the solvent removed by distillation. The residue was purified by flash chromatography on a silica gel column eluted with dichloromethane:petroleum ether (1:1) to give the novel compound 5′-fluoro-2′-(methylamino)acetophenone, m.p. 43°–45°.

(b) A mixture of acetic anhydride (4.6 ml) and formic acid (3.1 3 ml) was stirred at 60° for 2 hours and then cooled to 10°. 5′-Fluoro-2′-(methylamino)acetophenone (3.0 g) was then added and the mixture stirred overnight. The solution was cooled in an ice-bath and water (20 ml) added followed by aqueous sodium hydroxide (specific gravity 1.5) added dropwise to pH 10. The mixture was extracted with dichloromethane (3×30 ml) and the combined extracts dried over magnesium sulphate to give a solution of 2′-acetyl-4′-fluoro-N-methylformanilide.

(c) A solution of sulphuryl chloride (3.2 ml) in dichloromethane (20 ml) was added dropwise over a period of 10 minutes to the solution of 2'-acetyl-4'-fluoro-N-methylformanilide at 0° under a nitrogen atmosphere and the mixture stored overnight at 0 to 5°. Water (25 ml) was added whilst maintaining the temperature below 1 0°. The dichloromethane layer was separated, washed with water (1 25 ml) and dried over magnesium sulphate to give a solution of 2'-(2-chloroacetyl)-4'-fluoro-N-methylformanilide.

(d) A solution of benzoic acid (6.7 g) and triethylamine (9.9 ml) in dichloromethane (80 ml) was added to the solution of 2'-(2-chloroacetyl)-4'-fluoro-N-methylformanilide at 0°. The mixture was stirred at ambient temperature for 24 hours and then heated under reflux for 2 hours. The mixture was washed with water (2×50 ml) and dried over magnesium sulphate. The solvent was removed by distillation and the residue added to potassium carbonate (1.76 g) and dry dimethylformamide (30 ml). The mixture was heated under nitrogen at 60° for 6 hours. Further potassium carbonate (1.0 g) was added and the heating continued for 6 hours. The solvent was removed under reduced pressure at 60° C., the residue triturated with water (30 ml), and the solid collected by filtration to give the novel compound 6-fluoro-1-methyl-4-oxo-1,4-dihydroquinol-3-yl benzoate, m.p. 188°–190°.

(e) A mixture of 6-fluoro-1-methyl-4-oxo-1,4-dihydro-quinol-3-yl benzoate (1.90 g), piperidine (0.9 ml) and dry dichloromethane (50 ml) was stirred under nitrogen for 24 hours at ambient temperature. The solvent was removed by distillation and the residue triturated with diethyl ether (100 ml). The resultant solid was collected by filtration to give the novel compound 6-fluoro-3-hydroxy-1-methyl-4-quinolone, m.pp. 104°–106°.

(f) 6-Fluoro-3-hydroxy-1-methyl-4-quinolone (1.0 g) was added to a mixture of activated charcoal (0.5 g), aqueous sodium hydroxide (5M, 4 ml) and water (20 ml) and the resultant solution was heated to 40° and filtered. The stirred filtrate was cooled to 5° and methanesulphonyl chloride (3×2 ml) wad added over a period of 3 hours whilst maintaining the ppH at the about 9 by the addition of aqueous sodium hydroxide (5M). The resultant solid was collected by filtration, washed with water (2×10 ml) and crystallised from industrial methylateed spirit (30 ml) to give the novel compound 6-fluoro-1-methyl-4-oxo-1,4-dihydroquinol-3-yl methanesulphonate, m.p. 188°–189°.

EXAMPLE 8

(a) 7-Fluoro-3-hydroxy-1-methyl-4-quinolone (2.0 g), obtained as described in Example 3a–f, was added to a stirred suspension of sodium hydride (0.44 g of a 60% dispersion in mineral oil) in dry dimethylformaide (15 ml) under nitrogen at ambient temperature and the stirring continued for 15 minutes before cooling to 0°. A solution of allyl bromide (1.3 ml) indimethylformamide (15 ml) was added and stirring continued for 3.5 hours. Methanol (2 ml) was added and solvent removed from the mixture by evaporation under reduced pressure at 60°. Water (60 ml) was added to the residue and the mixture extracted with dichloromethane (3×100 ml). The combined extracts were dried over magnesium sulphate and the solvent was removed by distillawtion to leave a solid which was triturated with diethyl ether (30 ml) to give the novel compound 3-allyloxy-7-fluoro-1-methyl-4-quinolone, m.p. 158°–159°.

(b) 2,2,2-Trifluoroethanol (7.0 ml) was added to a stirred suspension of sodium hydride (4.0 g of a 50% dispersion in mineral oil) in dioxan (60 ml). After 30 minutes 3-allyloxy-7-fluoro-1-methyl-4-quinolone (2.8 g) was added and the mixture heated under reflux for 24 hours. The solvent was removed by evaporation under reduced pressure at 40°. The residue was dissolved in water (150 ml) and the solution extracted with dichloromethane (3×150 ml). The combined extracts were dried over magnesium sulphate and evaporated to give the novel compound 3-allyloxy-1-methyl-7-(2,2,2-trifluoroethoxy)-4-quinolone, m.p. 120°.

(c) A mixture of 3-allyloxy-1-methyl-7-(2,2,2-trifluoroethoxy)-4-cuinolone (2.40 g), tris(triphenylphosphine)rhodium chloride (200 mg) and aqueous industrial methylated spirit (60 ml, 90% industrial methylated spirit) was heated under reflux for 48 hours. Hydrochloric acid (5M, 5 ml) was added, the mixture stirred for 1hour and then evaporated to dryness. The residue was stirred with aqueous sodium hydroxide (5M, 10 ml) and filtered. The filtrate was neutralised with hydrochloric acid (5M, 10 ml) and the resultant solid collected by filtration to give the novel compound 3-hydroxy-1-methyl-7-(2,2,2-trifluoro-ethoxy)-4-quinolone, m.p. 151°.

(d) A mixture of 3-hydroxy-1-methyl-7-(2,2,2-trifluoroethoxy)-4-quinolone (0.40 g), aqueous sodium hydroxide (5M, 0.43 ml) and water (10 ml) was stirred under nitrogen at 0°. Methanesulphonyl chloride (0.25 g) was added with stirring and the pH adjusted to 9 with aqueous sodium hydroxide (5M, 0.5 ml). The resultant solid was collected by filtration, washed with water (10 ml) and crystallised from industrial methylated spirit (10 ml) to give the novel compound 1-methyl-4-oxo-7-(2,2,2-trifluoroethoxy)-1,4-dihydro-quinol-3-yl methanesulphonate, m.p. 110°–112°.

EXAMPLE 9

(a) A mixture of 4'-methyl-2'-chloroacetophenone and 4'-chloro-2'-methylacetophenone (98 g), [obtained by reaction of 3-chlorotoluene with acetyl chloride using the conditions of C R Noller and R Adams, J.Amer.Chem.Soc., 46, 1892 (1924)], methylamine (33% w/w solution in industrial methylated spirit, 130 ml), copper powder (3 g) and industrial methylated spirit (150 ml) was stirred in a sealed pressure vessel at 100° overnight. After cooling, further methylamine solution (130 ml) was added, the pressure vessel resealed and the mixture stirred at 100° overnight. The cooled mixture was washed out of the pressure vessel with industrial methylated spirit (2×200 ml) and then heated to 60°. Aqueous sodium sulphide nonahydrate (6.1 g in 60 ml water was added, the mixture stirred at 60° for 15 minutes and filtered through diatomaceous earth (sold under the trade name CELITE). The filter bed was washed with industrial methylated spirit (2×100 ml) and the combined filtrate and washings were evaporated to dryness under reduced pressure. The residue was stirred with hydrochloric acid (5M, 400 ml) for 2.75 hours and the resultant aqueous solution basified to pH 8 to 9 with aqueous sodium hydroxide (specific gravity 1.5). The mixture was extracted with dichloromethane (600 ml, then 2×400 ml), the combined extracts were dried over magnesium sulphate and the solvent was removed by distillation. The residue was dissolved in diethyl ether (500 ml) and the solution extracted with hydrochloric acid (5M, 3×150 ml). The diethyl ether solution was discarded. The aqueous extracts were basified to pH 8 with aqueous sodium hydroxide (specific gravity 1.5) and then extracted with diethyl ether (2×250 ml). The combined diethyl ether extracts were dried over magnesium sulphate and the solvent was removed by distillation. The residue was distilled under reduced pressure to give the novel compound 4'-methyl-2'-(methylamino)acetophenone, m.p. 47°.

(b) A mixture of acetic anhydride (23.3 ml) and formic acid (15.9 ml) was stirred at 50 to 60° for 90 minutes and then cooled to 0 to 5° in an ice/salt bath. 4'-Methyl-2'-(methylamino)acetophenone (17.25 g) was added and the solution stirred at 20° for 3 hours. The reaction mixture was cooled to 0° and water (80 ml) added dropwise whilst maintaining the temperature below 8°. Aqueous sodium hydroxide (specific gravity 1.5, 60 ml) was added dropwise whilst maintaining the temperature below 10°. The mixture was extracted with dichloromethane (3×30 ml). The combined extracts were washed with aqueous sodium chloride (6M, 100 ml) and dried over magnesium sulphate. The solvent was removed by distillation and the residue purified by flash chromatography on a silica gel column eluted with dichloromethane:methanol (100:1) to give the novel compound 2'-acetyl-5'-methyl-N-methylformanilide, m.p. 58°–60°.

(c) Sulphuryl chloride (10.9 ml) was added dropwise over 20 minutes to a solution of 2'-acetyl-5'-methyl-Nmethylformanilide (17.0 g) in dichloromethane (200 ml) at 0° and the resultant solution was then stirred for 4 hours at 0 to 5°. Water (100 ml) was added dropwise whilst maintaining the temperature below 0° using an ice/salt bath. The dichloromethane layer was separated, washed with water (100 ml) and dried over magnesium sulphate to give a solution of 2'-(2-chloro-acetyl)-5'-methyl-N-methylformanilide.

(d) A solution of benzoic acid (30.3 g) and triethylamine (50.1 ml) in dichloromethane (150 ml) was added dropwise at 0° over a period of 15 minutes to the solution of 2'-(2-chloroacetyl)-5'-methyl-N-methylformanilide obtained above. The resultant solution was allowed to warm to ambient temperature and then heated under reflux overnight. After cooling the reaction mixture was washed with water (2×200 ml), dried over magnesium sulphate and evaporated to give crude 2-[4-methyl-2-(N-methylformamido)phenyl]-2-oxoethyl benzoate.

(e) A mixture of the benzoate obtained above (8.7 g), potassium carbonate (4.85 g) and dimethylformamide (135 ml) was stirred at 60° for 24 hours. The cooled mixture was filtered and the solid residue washed with dimethylformamide (50 ml). The combined filtrate and washings were evaporated under reduced pressure at 60°. The residue was triturated with water (150 ml), then diethyl ether (100 ml) and then acetone (40 ml) to give the novel compound 1,7-dimethyl-4-oxo-1,4-dihydroquinol-3-yl benzoate, m.p. 200°–202°.

(f) A mixture of 1,7-dimethyl-4-oxo-1,4-dihydroquinol-3-yl benzoate (1.45 g), piperidine (0.49 ml) and dichloromethane (14 ml) was stirred at ambient temperature under nitrogen for 3 days. Further piperidine (0.13 ml) was added and the mixture stirred overnight. The solvent was removed by distillation and the residue triturated with diethyl ether (20 ml) to give the novel compound 3-hydroxy-1,7- dimethyl-4quinolone, m.p. 268°.

(g) Triethylamine (1.3 ml) was added to a stirred suspension of 3-hydroxy-1,7-dimethyl-4-quinolone (0.91g) and methanesulphonyl chloride (0.56 ml) in dichloromethane (30 ml) and the resultant solution stirred for 90 minutes. The solvent was removed by distillation and the residue crystallised from industrial methylated spirit (5 ml). The resultant crystals were triturated with water (5 ml) and dried to give the novel compound 1,7-dimethyl-4-oxo-],4-dihydroquinol-3-yl methanesulphonate, m.p. 139°–141°.

EXAMPLE 10

(a) A mixture of acetic anhydride (23 ml) and formic acid (15.5 ml) was stirred at 50° for 4 hours and then cooled to 0° in an ice/salt bath. 2'-(Ethylamino)-acetophenone (20.5 g) was added in small portions over 15 minutes and the mixture allowed to stand at room temperature for 1 hour. The mixture was cooled to 0° and water (100 ml) followed by aqueous sodium hydroxide (specific gravity 1.5, 10 ml) was added dropwise whilst maintaining the temperature below 10°. The resultant mixture was extracted with dichloromethane (4×100 ml) and the combined extracts were dried over magnesium sulphate to give a solution of 2'-acetyl-N-ethylformanilide.

(b) A solution of sulphuryl chloride (12.7 ml) in dichloromethane (20 ml) was added dropwise to the solution of 2'-acetyl-N-ethylformanilide at 0° and the mixture stirred at 0° for 4 hours. Water (110 ml) was then added whilst maintaining the temperature below 10°. The dichloromethane layer was separated, washed with water (110 ml) and aqueous sodium chloride (6M, 250 ml) and then dried over magnesium sulphate to give a solution of 2'-(2-chloroacetyl)-N-ethylformanilide.

(c) A solution of benzoic acid (43.4

(g) and triethylamine (72.3 ml) in dichloromethane (200 ml) was added dropwise over 20 minutes to the solution of 2'-(2-chloroacetyl)-N-ethylformanilide at 0°. The mixture was allowed to warm to ambient temperature overnight and then heated under reflux for 6 hours. After cooling, the reaction mixture was washed with water (3×250 ml), dried over magnesium sulphate and the solvent removed by distillation to give the novel compound 2-[2-(N-ethylformamido)phenyl]-2-oxoethyl benzoate, m.p. 78°–80°.

(d) A mixture of 2-[2-(N-ethylformamido)phenyl]-2-C oxoethyl benzoate (21.2 g), potassium carbonate (11.82 g) and dry dimethylformamide (330 ml) was stirred at 60° for 15 hours. The reaction mixture was filtered and the residue washed with dimethylformamide (150 ml). The combined filtrate and washings were evaporated under reduced pressure at 60° and the residue triturated with water (200 ml) and then with acetone (2×30 ml) to give the novel compound 1-ethyl-4-oxo-1,4-dihydroquinol-3-yl benzoate, m.p. 190°–192°.

(e) A mixture of 1-ethyl-4-oxo-1,4-dihydroquinol-3-yl benzoate (6.29 g), piperidine (2.1ml) and dichloromethane (60 ml) was stirred under nitrogen at ambient temperature for 3 days. Further piperidine (0.5 ml) was added and the mixture stirred for 24 hours. The solvent was removed by distillation and the residual solid triturated with diethyl ether (20 ml) to give the novel compound 1-ethyl-3-hydroxy-4-quinolone, m.p. 180°–182°.

(f) Triethylamine (5.6 ml) was added to a stirred suspension of 1-ethyl-3-hydroxy-4-quinolone (3.74 g) and methanesulphonyl chloride (2.3 ml) in dichloromethane (80 ml) and the resultant solution was stirred for 90 minutes. The solution was washed with water (50 ml) and dried over magnesium sulphate. The solvent was removed by distillation and the residue crystallised from industrial methylated spirit (10 ml) to give the novel compound 1-ethyl-4-oxo-1,4-dihydro-quinol-3-yl methanesulphonate, m.p. 141°–143°.

EXAMPLE 11

(a) A mixture of 3-allyloxy-7-fluoro-1-methyl-4quinolone (2.1 g), prepared as described in Example 8(a), sodium methoxide (3 g) and dry methanol (50 ml) was heated under reflux for 4 days. Methanolic hydrochloric acid was added to neutralise the solution and tris(triphenylphosphine)rhodium chloride (0.2 g) was added. The mixture was heated under reflux for 3 days and then acidified with methanolic hydrochloric acid to pH 1. The solvent was removed by distillation under reduced pressure and the residue stirred with aqueous sodium hydroxide (0.5M, 50 ml) and filtered. The filtrate was neutralised with hydrochloric acid (5M, 5 ml), the precipitate was collected by filtration and washed with water (2×10 ml) to give the novel compound 3-hydroxy-7-methoxy-1-methyl-4-quinolone, m.p. 228°.

(b) Methanesulphonyl chloride (0.88 ml) was added to a stirred suspension of 3-hydroxy-7-methoxy-1-methyl-4quinolone (0.7 g) and triethylamine (2.4 ml) in dry dichloromethane (100 ml) at ambient temperature and the resultant solution stirred for 3 hours. Water (50 ml) was added and the layers separated. The dichloromethane layer was dried over magnesium sulphate and the solvent evaporated. The residue was purified by flash chromatography on a silica gel column eluted with dichloromethane:methanol (19:1) followed by crystallisation from acetonitrile:methanol (20:1, 10 ml) to give the novel compound 7-methoxy-1-methyl-4-oxo-1,4-dihydroquinol-3-yl methanesulphonate, m.p. 163°.

EXAMPLE 12

Ethanesulphonyl chloride (1.5 ml) was added to a stirred mixture of 7-fluoro-3-hydroxy-1-methyl-4quinolone (3.0 g), obtained as described in Example 3a-f, triethylamine (4.35 ml) and dry dichloromethane (100 ml) at ambient temperature and the resultant solution stirred for 5 minutes then kept at ambient temperature overnight. Further ethanesulphonyl chloride (0.2 ml) was added and the solution stirred at ambient temperature for 4 hours and then kept at this temperature for 3 days. The mixture was filtered and the filtrate was washed with water (2×150 ml). The dichloromethane solution was dried over magnesium sulphate and the solvent evaporated to give a residue which was crystallised from industrial methylated spirit (100 ml). The solid was triturated with diethyl ether (100 ml) and then water (500 ml) to give the novel compound 7-fluoro-1-methyl-4-oxo-1,4-dihydro-quinol-3-yl ethanesulphonate, m.p. 154°-156.5°.

EXAMPLE 3

(a) A mixture of potassium hydroxide (50.4 g), 4-chloro-7-trifluoromethylquinoline-1-oxide (21.8 g) and industrial methylated spirit (800 ml) was heated under reflux for 150 minutes. The solvent was evaporated, the residue was triturated with water (600 ml) and filtered. The filtrate was neutralised with glacial acetic acid (150 ml) with cooling and the resultant precipitate collected by filtration, washed with water (50 ml) and dried. The crude product was crystallised from methanol to give the novel compound 4-hydroxy-7-trifluoromethyl-quinoline-1-oxide, m.p. 208°-210°.

(b) A mixture of 4-hydroxy-7-trifluoromethyl-quinoline-1-oxide (2.0 g), methanesulphonic anhydride (1.7 g) and potassium carbonate (1.3 g) in dichloromethane (100 ml) was stirred at 0° for 2 hours. Further methanesulphonic anhydride (1.7 g) and potassium carbonate (1.3 g) were then added and the mixture was stirred at ambient temperature overnight. Water (50 ml) was added and the precipitated solid collected by filtration to give a first crop of the novel compound 4-hydroxy-7-trifluoromethylquinol-3-yl methanesulphonate, m.p. 220°. The dichloromethane layer of the filtrate was separated and the aqueous layer subsequently extracted with dichloromethane (2×25 ml). The combined dichloromethane layer and extracts were evaporated to dryness. The residue was purified by flash chromatography on a silica gel column eluted with dichloromethane:methanol (20:1) to give a second crop of 4-hydroxy-7-trifluoromethylquinol-3-yl methanesulphonate, m.p. 220°.

(c) Dimethyl sulphate (26.1ml) was added to a stirred suspension of 4-hydroxy-7-trifluoromethylquinol-3-yl methanesulphonate (7.19 g) and potassium carbonate (75.5 g) in dry 2-butanone (350 ml) and the resultant mixture was heated under reflux for 5 hours. The solvent was removed by distillation and the resultant residue was extracted with dichloromethane (600 ml then 400 ml). The combined extracts were dried over magnesium sulphate and the solvent was removed by distillation. The residue was purified by flash chromatography on a silica gel column eluted with dichloromethane:methanol (75:1) followed by flash chromatography on a silica gel column eluted with ethyl acetate and crystallisation from industrial methylated spirit (150 ml) to give the novel compound 1-methyl-4-oxo-7-trifluoromethyl-1,4-dihydroquinol-3-yl methanesulphonate, m.p. 218°.

EXAMPLE 14

(a) A mixture of 3-allyloxy-7-fluoro-1-methyl-4quinolone, obtained as described in Example 8a, (2.3 g), potassium cyanide (1.0 g), 18-crown-6 ether (5.0 g) and dimethylformamide (200 ml) was stirred at 95° for 2 days. After cooling to ambient temperature, the mixture was poured into water (600 ml) and extracted with dichloromethane (3×150 ml). The combined extracts were washed with water (2×200 ml), dried over magnesium sulphate and the solvent was removed by distillation. The residue was triturated with diethyl ether (50 ml) and the resultant solid added to a mixture of potassium cyanide (1.0 g), 18-crown-6 ether (5.0 g) and dimethylformamide (200 ml). The resultant solution was stirred at 140° for 16 hours and then allowed to cool to 60°. The solvent was removed under reduced pressure at 60° and the residue was partitioned between water (100 ml) and dichloromethane (200 ml). The dichloromethane solution was dried over magnesium sulphate and filtered through silica gel (30 g). The filter bed was washed with dichloromethane (5×100 ml) and the combined filtrate and washings were evaporated to give crude 3-allyloxy-7-cyano 1-methyl-4-quinolone.

(b) A mixture of the crude 3-allyloxy-7-cyano-1-methyl-4-quinolone (1.2 g), tris(triphenylphosphine)rhodium chloride (0.1 g) and ethanol (200 ml) was heated under reflux for 2 days. Hydrochloric acid (1M, 10 ml) was added, the mixture heated under reflux for 2 hours and then the solvent was evaporated under reduced pressure at 50°. The residue was extracted with aqueous sodium hydroxide (1M, 50 ml) and the extract neutralised with hydrochloric acid (12M, 4 ml). The resultant solid was collected by filtration and washed with water (10 ml) t give the novel compound 7-cyano-3-hydroxy-1-methyl-4-quinolone, m.p. 305°.

(c) Methanesulphonyl chloride (1.0 ml) was added to a stirred suspension of 7-cyano-3-hydroxy-1-methyl- 4quinolone (0.4 g) and triethylamine (2.0 ml) in dry dichloromethane (200 ml) at 0 to 5° and the resultant solution stirred for 2 hours. The solution was washed with water (2×50 ml), dried over magnesium sulphate and the solvent removed by distillation. The residue was purified by flash chromatography on a silica gel column eluted with dichloromethane:methanol (40:1) followed by trituration with diethyl ether (10 ml) to give the novel compound 7-cyano-1-methyl-4-oxo-1,4-dihydroquinol-3-yl methanesulphonate, m.p. 268°.

EXAMPLE 15

(a) A mixture of 3-allyloxy-7-fluoro-1-methyl-4quinolone, obtained as described in Example 8a, (8.0 g), sodium thiomethoxide (5.0 g) and dimethylformamide (200 ml) was stirred at ambient temperature overnight and then at 60° for 6 hours. Hydrochloric acid (5M, 20 ml) was added and the solvent was removed under reduced pressure at 60°. The residue was extracted with industrial methylated spirit (2×100 ml) to give a solution of 3-allyloxy-]-methyl-7-methylthio-4-quinolone in industrial methylated spirit.

(b) Tris(triphenylphosphine)rhodium chloride (0.1 g) was added to the solution of 3-allyloxy-1-methyl-7-methylthio-4-quinolone and the mixture heated under reflux for 2 days. Hydrochloric acid (5M, 20 ml) was added dropwise and the mixture heated under reflux for 2 hours. The solvent was evaporated under reduced pressure at 50° and the resultant residue extracted with aqueous sodium hydroxide (1M, 100 ml). The extract was neutralised with hydrochloric acid (5M, 20 ml) and the solid was collected by filtration. The solid was washed with water (50 ml) and dried to give the novel compound 3-hydroxy-1-methyl-7-methylthio-4quinolone, m.p. 237°.

(c) Methanesulphonyl chloride (2.2 ml) was added to a stirred suspension of 3-hydroxy-1-methyl-7-methylthio-4-quinolone (4.2 g) and triethylamine (5.28 ml) in dry dichloromethane (200 ml) at 0 to 5° and the resultant solution stirred for 2 hours. Further triethylamine (5.28 ml) and methanesulphonyl chloride (2.2 ml) were added and stirring was continued overnight at ambient temperature. The solution was washed with water (2×100 ml) and dried over magnesium sulphate. The solvent was removed by distillation and the residue crystallised from industrial methylated spirit (300 ml) then recrystallised from industrial methylated spirit (300 ml) to give the novel compound 1-methyl-7-methylthio-4-oxo-1,4-dihydroquinol-3-yl methanesulphonate, m.p. 182°.

EXAMPLE 16

A solution of m-chloroperoxybenzoic acid (0.98 g, 55% purity) in dichloromethane (150 ml) was dried over magnesium sulphate and the filtered solution cooled to 0°. 1-Methyl-7-methylthio-4-oxo-1,4-dihydroquinol-3-yl methanesulphonate (0.94 g), obtained as described in Example 15, was added and the resultant solution stirred at 0° for 2 hours. The solution was washed with aqueous sodium sulphite (1M, 15 ml) then aqueous sodium bicarbonate (1M, 50 ml) and dried over magnesium sulphate. The solvent was removed by distillation and the residue purified by flash chromatography on a silica gel column eluted with dichloromethane:methanol (10:1) followed by crystallisation from industrial methylated spirit (50 ml) to give the novel compound 1-methyl-7-methylsulphinyl-4-oxo-1,4-dihydroquinol-3-yl methanesulphonate, m.p. 248°.

EXAMPLE 17

1-Methyl-7-methylthio-4-oxo-1,4-dihydroquinol-3-yl methananesulphonate (0.46 g), obtained as described in Example 15, was added to a solution of m-chloroperoxybenzoic acid (1.0 g, 55% purity) in dichloromethane (200ml), previously dried over magnesium sulphate, and the mixture stirred overnight at ambient temperature. Dichloromethane (300 ml) was added and the resultant solution washed with aqueous sodium sulphite (1M, 20 ml) then aqueous sodium bicarbonate (1M, 100 ml) and dried over magnesium sulphate. The solvent was removed by distillation and the residue crystallised from dichloromethane:diethyl ether (1:5, 120 ml) and then from industrial methylated spirit (100 ml) to give the novel compound 1-methyl-7-methylsulphonyl-4-oxo-1,4-dihydroquinol-3-yl methanesulphonate, m.p. 258°–260°.

EXAMPLE 18

(a) The solvent was removed by distillation from a solution of 2'-(2-chloroacetyl)-N-methylformanilide, obtained as described in Example 2(c), and the resultant oil purified by high pressure liquid chromatography on a silica column eluted with dichloromethane:methanol (100:1). The 2'-(2-chloroacetyl)-N-methylformanilide (5.0 g) was added to a solution of silver methanesulphonate (10 g) in dry acetonitrile (200 ml) and the mixture was heated at 60 to 65° for 5 days in the dark. The cooled mixture was filtered and the filtrate evaporated under reduced pressure at 40°. The residue was extracted with dichloromethane (50 ml) and filtered through diatomaceous earth (sold under the trade name CLARCEL). The solvent was removed by distillation from the filtrate and the residue purified by high pressure liquid chromatography on a silica column eluted with dichloromethane:methanol (100:1) to give the novel compound 2-[2-(N-methylformamido)phenyl]-2-oxoethyl methanesulphonate, m.p. 67°–69°. The product may be crystallised from industrial methylated spirit:diethyl ether (1:10) to give 2-[2-(N-methylformamido)phenyl-2-oxoethyl methanesulphonate, m.p. 74.5°–75°.

(b) Molecular sieves (0.75 g, 4A°, activated and ground) were added to a solution of 2-[2-(N-methylformamido)phenyl]-2-oxethyl methanesulphonate (0.10 g) in toluene (50 ml) at 50° and the resultant mixture was stirred at 50° overnight. 1,8-Diazabicyclo[5.4.0]-undec-7-ene (0.25 ml) was added, the mixture stirred for 4 hours at 50°, then filtered and the solvent removed from the filtrate under reduced pressure at 50°. The residue was triturated with industrial methylated spirit (2 ml) and the resultant solid washed with industrial methylated spirit (2×1 ml) to give the novel compound 1-methyl-4-oxo-1,4-dihydroquinol-3 -yl methanesulphonate, m.p. 206°–208°.

EXAMPLE 19

A solution of 2'-(2-chloracetyl)-N-methylformanilide (3.3 g) in dichloromethane (20 ml), obtained as described in Example 2 (c), was added dropwise over a period of 15 minutes to a stirred solution of aqueous sodium hydroxide (1M, 31ml) whilst maintaining the temperature at 15°. The mixture was stirred for 5 minutes at 15°, the aqueous phase was separated and washed with dichloromethane (25 ml). Hydrochloric acid (5M, 6 ml) was added to the aqueous phase at 0° and the resultant precipitate collected by filtration and washed with water (3×20 ml) to give 3-hydroxy-1-methyl-4-quinolone, m.p. 235°–240°.

(b) The 3-hydroxy-1-methyl-4-quinolone can be similarly treated as previously disclosed in Example 1(g) to give 1-methyl-4-oxo-1,4-dihydroquinol-3-yl methanesulphonate.

EXAMPLE 20

(a) Sodium methoxide (17.75 g) was added to a stirred solution of 2-[2-(N-methylformamido) phenyl]-2-oxoethyl benzoate, obtained as described in Example 2a–d, (186 g) in dichloromethane (1300 ml) at 0° under nitrogen resulting in an exotherm to 25 to 30°. The mixture was recooled at 0° and a second portion of sodium methoxide (17.75 g) added resulting in a further exotherm and the resultant mixture stirred for 1 hour. Sodium methoxide (35.5 g) was then again added in two equal portions and the resultant mixture stirred at 0 to 10° for 1 hour. Water (1860 ml) was added over 70 minutes maintaining the temperature below 6°. The phases were separated and the dichloromethane phase was extracted with aqueous sodium hydroxide (0.5M, 930 ml). The combined aqueous phase and extract were washed with dichloromethane (930 ml) and then cooled to 0°. Hydrochloric acid (5M, 300 ml) was added dropwise to pH 3 to 4 followed by aqueous sodium hydroxide (5M, 38 ml) and then aqueous sodium bicarbonate (1M, 250 ml) to pH 8. The resultant solid was collected by filtration and washed with water (3×200 ml) to give 3-hydroxy-1-methyl-4-quinolone, m.p. 239°–241°.

(b) The 3-hydroxy-1-methyl-4-quinolone can be similarly treated as previously disclosed in Example 1(g) to give 1-methyl-4-oxo-1,4-dihydroquinol-3-yl methanesulphonate.

EXAMPLE 21

(a) A solution of 1-[4-chloro-2-(methylamino)phenyl-2-methylsulphinylethanone (17 g) in a mixture of glacial acetic acid (35 ml) and absolute ethanol (35 ml) was added dropwise over 20 minutes to a stirred suspension of zinc dust (22.5 g) in acetic acid (20 ml) and absolute ethanol (35 ml) under nitrogen at ambient temperature. After stirring at ambient temperature for 24 hours, the reaction mixture was filtered through diatomaceous earth (sold under the trade name CELITE) and the filter bed was washed with glacial acetic acid (200 ml). Water (600 ml) was added to the combined filtrate and washing and the mixture was extracted with dichloromethane (3×200 ml). The combined extracts were dried over magnesium sulphate and the solvent was removed by distillation to give the novel compound 4'-chloro-2'-(methylamino)acetophenone, m.p. 65°–66°.

(b) A mixture of acetic anhydride (12 ml) and formic acid (8 ml) was heated at 55° for 3 hours and then cooled to ambient temperature. 4'-Chloro-2'-(methylamino)acetophenone (9.7 g) was then added and the mixture stirred at ambient temperature overnight. Water (40 ml) was added and the mixture stirred in an ice/salt bath and neutralised by adding aqueous sodium hydroxide (specific gravity 1.5, 22 ml) whilst maintaining the temperature below 30°. The reaction mixture was extracted with dichloromethane (3×50 ml) and the combined extracts were dried over magnesium sulphate to give a solution of 2'-acetyl-5'-chloro-N-methylformanilide.

(c) A solution of sulphuryl chloride (9 ml) in dichloromethane (15 ml) was added dropwise to the solution of 2'-acetyl-5'-chloro-N-methylformanilide under nitrogen whilst maintaining the temperature at 0 to Water (40 ml) was then added dropwise whilst maintaining the temperature at 0 to 10°. The mixture was stirred for a further 5 minutes and then the dichloromethane layer was separated and dried over magnesium sulphate to give a solution of 5'-chloro-2'-(2-chloroacetyl)-N-methylformanilide.

(d) A solution of benzoic acid (18.8 g) in triethylamine (28.5 ml) and dichloromethane (110 ml) at 0° was added dropwise over 1 hour to the solution of 5'-chloro-2'-(2-chloroacetyl)-N-methylformanilide at 0° under nitrogen. The mixture was stirred for a further hour whilst maintaining the temperature at 0 to 5° and then heated under reflux overnight. After cooling, the reaction mixture was washed with water (2×100 ml), dried over magnesium sulphate, and the solvent removed by distillation to give the novel compound 2-[4-chloro-2-(N-methylformamido)phenyl]-2-oxoethyl benzoate in the form of a gum.

(e) A mixture of the crude 2-[4-chloro-2-(N-methylformamido)phenyl]-2-oxoethyl benzoate (6.67 g), potassium carbonate (3.2 g) and dry dimethylformamide (100 ml) was stirred at ambient temperature overnight and then at 60° for 5 hours. The solvent was removed by evaporation under reduced pressure, the residue triturated with water (3×200 ml) and then with diethyl ether (50 ml) and the solid was collected to give the novel compound 7-chloro-1-methyl-4-oxo-],4-dihydroquinol-3-yl benzoate, m.p. 191°–194°.

(f) A mixture of 7-chloro-1-methyl-4-oxo-1,4-dihydro-quinol-3-yl benzoate (3.45 g), piperidine (1.2 ml) and dichloromethane (100 ml) was stirred at ambient temperature for 2.5 days. The solvent was removed by distillation and the residue triturated with diethyl ether (100 ml) to give the novel compound 7-chloro-3-hydroxy-1-methyl-4-quinolone, m.p. 225°–228°.

(g) Triethylamine (3 ml) was added to a stirred mixture of 7-chloro-3-hydroxy-1-methyl-4-quinolone (2.31g), methanesulphonyl chloride (1.3 ml) and dichloromethane (70 ml) and the resultant solution stirred for 90 minutes. The solvent was removed by distillation and the residue crystallised from industrial methylated spirit (30 ml) and the solid triturated with diethyl ether (50 ml) to give the novel compound 7-chloro-1-methyl-4-oxo-1,4-dihydroquinol-3-yl methanesulphonate, m.p. 157°–158°.

EXAMPLE 22

(a) A solution of 1-[4,5-difluoro-2-(methylamino)-phenyl]-2-methylsulphinylethanone (32.4 g) in acetic acid (90 ml) and ethanol (90 ml) was added over a period of 20 minutes to a stirred suspension of zinc dust (50 g) in acetic acid (45 ml) and ethanol (80 ml) at 0° under nitrogen. The mixture was stirred at ambient temperature overnight and then filtered through diatomaceous earth (sold under the trade name CELITE). The filter bed was washed with acetic acid (3×50 ml). The combined filtrate and washings were poured into water (1200 ml) and the mixture was extracted with dichloromethane (3×400 ml). The combined extracts were washed with aqueous sodium carbonate (1M, 2×500 ml) and dried over magnesium sulphate. The solvent was removed by distillation to give the novel compound 4',5'-difluoro-2'-(methylamino)acetophenone, m.p 51°–52°.

(b) A mixture of acetic anhydried (23 ml) and formic acid (98%, 15.5 ml) was stirred at 50 to 60° for 1 hour and then cooled to ambient temperature. 4',5'-Difluoro- 2,-(methylamino)acetophenone (20.4 g) was added whilst maintaining the temperature below 20° in an ice/water bath. The mixture was stirred at ambient temperature overnight and then cooled to 0°. Water (100 ml) followed by aqueous sodium hydroxide (specific gravity 1.5, 60 ml) was added whilst maintaining the temperature below 10°. The mixture was extracted with dichloromethane (4×150 ml) and the combined extracts were washed with aqueous sodium carbonate (1M, 100 ml) and dried over magnesium sulphate to give a solution of 2'-acetyl-4',5'-difluoro-N-methylformanilide.

(c) A solution of sulphuryl chloride (13.3 ml) in dichloromethane (40 ml) was added dropwise over 30 minutes to the solution of 2'-acetyl-4',5'-difluoro-Nmethylformanilide at 0° under nitrogen and the solution stirred at 0° for 3.5 hours. Water (100ml) was added dropwise whilst maintaining the temperature at 0 to 10°. The dichloromethane layer was separated, washed with water (100ml) and dried over magnesium sulphate to give a solution of 2'-(2-chloroacetyl)-4',5'-difluoro-N-methylformanilide.

(d) A solution of benzoic acid (40.3 g) and triethylamine (61 ml) in dichloromethane (200 ml) was added dropwise over 20 minutes to the solution of 2'-(2-chloroacetyl)-4',5'-difluoro-N-methylformanilide at 0° under nitrogen and the resultant solution stirred overnight at ambient temperature. The mixture was washed with water (3×250 ml) and the solvent removed by distillation. The residue was purified by flash chromatography on a silica gel eluted with dichloromethane:methanol (50:1) to give the novel compound 2-[4,5-difluoro-2-(N-methylformamido)phenyl-2-oxoethyl benzoate in the form of an oil.

(e) Sodium methoxide (4.37 g) was added to a solution of 2-[4,5-difluoro-2-(N-methylformamido)phenyl]-2oxoethyl benzoate (11.2 g) in dichloromethane (840 ml) at 0° under nitrogen and the mixture stirred for 90 minutes. The mixture was extracted with water (1l) and then aqueous sodium hydroxide (5M, 2×100 ml). The combined extracts were acidified with hydrochloric acid (5M, 250 ml). The precipitate was collected by filtration and washed with water (100 ml) to give the novel compound 6,7-difluoro-3-hydroxy-l-methyl-4quinolone, m.p. 264°–265°.

(f) Triethylamine (7.0 ml) was added to a stirred suspension of 6,7-difluoro-3-hydroxy-1-methyl-4quinolone (5.26 g) and methanesulphonyl chloride (2.9 ml) in dichloromethane (200 ml) at 0 to 5° and the resultant solution stirred for 90 minutes. The solution was washed with water (150 ml), dried over magnesium sulphate and the solvent removed by distillation. The residue was purified by flash chromatography on a silica gel column eluted with dichloromethane:methanol (40:1) followed by trituration with diethyl ether (100 ml) to give the novel compound 6,7-difluoro-1-methyl-4-oxo-1,4-dihydroquinol-3-yl methanesulphate, m.p. 202°–204°.

EXAMPLE 23

(a) Iodomethane (14 ml) was added to a stirred mixture of 2'-amino-4',5'-dimethoxyacetophenone (40 g), potassium carbonate (31.2 g) and dry dimethylformamide (200 ml) and the mixture stirred at ambient temperature for 40 hours. The solvent was evaporated under reduced pressure and the residue triturated with dichloromethane (250 ml). The mixture was filtered and the filter bed washed with dichloromethane (50 ml). The combined filtrate and washing were evaporated and the residue purified by flash chromatography on a silica gel column eluted with dichloromethane:industrial methylated spirit (99:1then 49:1) followed by trituration with diethyl ether (400 ml then 100 ml) to give the novel compound 4',5'-dimethoxy-2'-(methylamino)acetophenone, m.p. 121°–123.5°.

(b) A mixture of acetic anhydride (24 ml) and formic acid (98%, 12 ml) was stirred at 60° for 90 minutes and then cooled to 5°. 4',5'-Dimethoxy-2'-(methylamino)-acetophenone (6.45 g) was added over a period of 10 minutes whilst maintaining the temperature below 10° in an ice/water bath. The mixture was stirred at 5° for 60 minutes and then allowed to warm to ambient temperature and stirred for a further 90 minutes. Water (100 ml) was added followed by slow addition of aqueous sodium hydroxide (specific gravity 1.5, 45 ml) whilst maintaining the temperature below 10°. The mixture was extracted with dichloromethane (3×100 ml) and the combined extracts were washed with aqueous sodium bicarbonate (1M, 100 ml), dried over magnesium sulphate and the solvent removed by evaporation. The residue was triturated with diethyl ether (100 ml, then 50 ml) to give the novel compound 2'-acetyl-4',5'-dimethoxy-N-methylformanilide, m.p. 133.5°–135.5°.

(c) Bromine (1.57 ml) was added dropwise over a period of 5 minutes to a stirred solution of 2'-acetyl-4',5'-dimethoxy-N-methylformanilide (7.13 g) in glacial acetic acid (35 ml) at ambient temperature. The mixture was stirred for 45 minutes and then diluted with dichloromethane (350 ml) before washing with saturated aqueous sodium sulphite (175 ml) then aqueous sodium bicarbonate (1M, 350 ml). The mixture was dried over magnesium sulphate and the solvent was removed by evaporation to give crude 2'-(2-bromoacetyl)-4',5'-dimethoxy-N-methylformanilide.

(d) A mixture of 2'-(2-bromoacetyl)-4',5'-dimethoxy-Nmethylformanilide (8.2 g), anhydrous sodium acetate (2.7 g) and dry dimethylformamide (35 ml) was stirred at ambient temperature for 4 hours. The mixture was filtered and the filter bed washed with dry dimethylformamide (10 ml). The combined filtrate and washing were evaporated under reduced pressure and the residue purified by flash chromatography on a silica gel column eluted with dichloromethane:industrial methylated spirit (40:1) to give the novel compound 2-[4,5-dimethoxy-2-(N-methylformamido)phenyl]-2-oxoethyl acetate in the form of an oil.

(e) Sodium methoxide (1.63 g) was added to a stirred solution of 2-[4,5-dimethoxy-2-(N-methylformamido)phenyl]-2-oxoethyl acetate (4.35 g) in dichloromethane (50 ml) at 0 to 5°. The mixture was stirred for 45 minutes at this temperature then for a further 75 minutes whilst warming to ambient temperature. The mixture was extracted with water (100 ml), aqueous sodium hydroxide (1M, 50 ml) and then water (50 ml). The combined extracts were washed with dichloromethane (50 ml), then cooled to 0 to 5° and methanesulphonyl chloride (3.4 ml) added. The mixture was stirred at 0 to 5° for 55 minutes after which time aqueous sodium hydroxide (5M, 10 ml) and then more methanesulphonyl chloride (1.7 ml) were added. After stirring for a further 30 minutes the precipitate wa collected, washed with water (20 ml) and crystallised from industrial methylated spirit (40 ml) to give the novel compound 6,7-dimethoxy-1-methyl-4-oxo-1,4-dihydro-quinol-3-yl methanesulphonate, m.p. 216°–217°.

EXAMPLE 24

(a) A solution of m-chloroperoxybenzoic acid (17 g, 55% purity) in dichloromethane (100 ml) was dried over magnesium sulphate and the filtered solution added dropwise to a solution of 4-chloro-7-trifluoromethoxyquinoline (16 g) in dichloromethane (100 ml) at 0°. The mixture was stirred at 0° for 4 hours and then at ambient temperature overnight. The solution was washed with saturated aqueous sodium carbonate (3×100 ml), dried over magnesium sulphate and the solvent removed by evaporation. The solid was triturated with diethyl ether:petroleum ether (b.p. 40°-60°) (50:50) to give the novel compound 4-chloro-7-trifluoromethoxyquinoline-1-oxide, m.p. 115°-116°.

(b) 4-Chloro-7-trifluoromethoxyquinoline-1-oxide (9.4 g) and potassium hydroxide (20.0 g) were dissolved in industrial methylated spirit (320 ml) and the solution was heated under reflux for 90 minutes. The solvent was removed by evaporation and the residue dissolved in water (100 ml). Glacial acetic acid (40 ml) was added at 0 to 5°, the precipitate collected, washed with water (2×10 ml) and crystallised from methanol (120 ml) to give the novel compound 4-hydroxy-7-trifluoromethoxyquinoline-1-oxide, m.p. 80°-181°.

(c) Methanesulphonic anhydride (1.55 g) was added to a stirred mixture of 4-hydroxy-7-trifluoromethoxyquinoline-1-oxide (2.0 g), potassium carbonate (1.2 g) and dichloromethane (100 ml) at 0°. After stirring at 0° for a further 2.5 hours, the reaction mixture was washed with saturated aqueous sodium carbonate (60 ml) and the dichloromethane phase separated. The aqueous phase was extracted with dichloromethane (2×50 ml) and the combined dichloromethane phase and extracts were dried over magnesium sulphate. The solvent was removed by evaporation and water (100 ml) followed by saturated aqueous sodium bicarbonate (5 ml) at 10° was added. The solid was collected by filtration to give the novel compound 4-hydroxy-7-trifluoromethoxyquinol-3-yl methanesulphonate, m.p. 125°-127°.

(d) Dimethyl sulphate (0.5 ml) was added to a stirred suspension of 4-hydroxy-7-trifluoromethoxyquinol-3-yl methanesulphonate (1.34 g) and potassium carbonate (1.4 g) in 2-butanone (50 ml) at ambient temperature. The mixture was heated under reflux for 2.5 hours and then cooled to ambient temperature. Aqueous ammonia (specific gravity 0.88, 1ml) was added and the mixture stirred for 30 minutes. Solvent was evaporated and the residue partitioned between water (50 ml) and dichloromethane (50 ml). The dichloromethane phase was dried over magnesium sulphate and the filtered solution purified by flash chromatography on a silica gel column eluted with dichloromethane:industrial methylated spirit (9:1) to give the novel compound ]-methyl-4-oxo-7-trifluoromethoxy-],4-dihydroquinol-3-yl methanesulphonate, m.p. 190°-191°.

EXAMPLE 25

2-Propanesulphonyl chloride (1.74 ml) was added to a stirred mixture of 7-fluoro-3-hydroxy-1-methyl-4quinolone (3.0 g), obtained as described in Example 3 a-f, triethylamine (4.35 ml) and dry dichloromethane (180 ml) and the mixture stirred at ambient temperature for 24 hours. Further quantities of 2-propanesulphonyl chloride (1.75 ml then 1 ml) and triethylamine (4.35 ml then 2.5 ml) were added after stirring for 24 hours and 48 hours respectively. After stirring for a further 24 hours, the mixture was filtered and the filter bed was washed with dichloromethane (30 ml). The combined filtrate and washing were washed with water (200 ml), saturated aqueous sodium bicarbonate (2×200 ml), then water (200 ml) and then dried over magnesium sulphate. The dichloromethane was removed by distillation to give a residue which was purified by flash chromatography on a silica gel column eluted with dichloromethane: industrial methylated spirit (19:1) followed by crystallisation from 2-propanol (25 ml) to give the novel compound 7-fluoro-1-methyl-4-oxo-1,4-dihydroquinol-3-yl 2-propanesulphonate, m.p. 130°-133°.

EXAMPLE 26

(a) A solution of m-chloroperoxybenzoic acid (3.01 g, 55% purity) in dichloromethane (40 ml) was dried over magnesium sulphate and the filtered solution was added to a stirred solution of 4-chloro-7-phenylquinoline (2.3 g) in dichloromethane (40 ml) at ambient temperature. Stirring was continued at ambient temperature overnight. The reaction mixture was washed with saturated aqueous sodium carbonate (2×180 ml), then with saturated aqueous sodium chloride (150 ml) and dried over magnesium sulphate. The solvent was removed by distillation to give the novel compound 4-chloro-7-phenylquinoline-1-oxide, m.p. 150°-153.5°.

(b) A solution of 4-chloro-7-phenylquinoline-1-oxide (1.9 g) and potassium hydroxide (4.2 g) in industrial methylated spirit (70 ml) was heated under reflux for 3 hours. The solvent was removed by distillation and water (200 ml) was added. The mixture was filtered and the filtrate neutralised with glacial acetic acid (5 ml). The precipitate was collected by filtration and purified by crystallisation from industrial methylated spirit (100 ml) to give the novel compound '4-hydroxy-7-phenylquinoline-1-oxide, m.p. 244°-250° decomp.

(c) A solution of methanesulphonic anhydride (3.05 g) in dichloromethane (10 ml) was added to a mixture of 4-hydroxy-7-phenylquinoline-1-oxide (3.28 g), potassium carbonate (2.13 g) and dichloromethane (160 ml) at 0°, the mixture was stirred at 0° for 2 hours, then allowed to warm to room temperature. Water (250 ml) was added, the layers were separated and the aqueous layer was extracted with dichloromethane (3×100 ml). The combined dichloromethane layer and extracts were dried over magnesium sulphate and the solvent was removed by distillation. The residue was subjected to flash chromatography on two successive silica gel columns eluted with dichloromethane: industrial methylated spirit (19:1) to give crude 4-hydroxy-7-phenylquinol-3-yl methanesulphonate.

(d) Dimethyl sulphate (0.4 ml) was added to a mixture of the crude 4-hydroxy-7-phenylquinol-3-yl methanesulphonate (1.0 g) and potassium carbonate (0.52 g) in 2-butanone (50 ml) at ambient temperature and the mixture then heated under reflux overnight. Aqueous ammonia (specific gravity 0.88, 2 ml) was added and after 60 minutes solvent was removed by distillation. The residue was dissolved in dichloromethane (100 ml), the solution washed with water (2×100 ml) and dried over magnesium sulphate. The dichloromethane was removed by distillation and the residue stirred with dichloromethane:industrial methylated spirit (2:1, 5 ml). The solid was collected by filtration and washed with dichloromethane (5 ml.) to give the novel compound 1-methyl-4-oxo-7-phenyl-],4-dihydroquinol-3-yl methanesulphonate, m.p. 221°-224°.

EXAMPLE 27

(a) Reaction of 1-chloro-4-fluorobenzene with acetyl chloride as described by E. D. Bergmann and S. Berkovic, J. Org. Chem., 26, 919 (1961), gave a product shown to be an inseparable mixture of 2'-chloro-5'-fluoroacetophenone and 5'-chloro-2'fluoroacetophenone.

(b) The mixture of 2'-chloro-5'-fluoroacetophenone and

5'-chloro-2'-fluoroacetophenone (67.6 g) was stirred with methylamine (33% w/w in industrial methylated spirit, 102 ml), copper powder (1g) and industrial methylated spirit (200 ml) at 80° overnight in a sealed pressure vessel. The cooled contents of the pressure vessel were added to a solution of sodium sulphide nonahydrate (3.5 g) in water (36 ml) at 65°. The mixture was stirred for 15 minutes, cooled and filtered through diatomaceous earth (sold under the trade name CELITE). The filter bed was washed with industrial methylated spirit (500 ml) and the combined filtrate and washing were evaporated under reduced pressure. Hydrochloric acid (5M, 250 ml) was added to the residue, stirred for 3.5 hours, the mixture was basified to pH 8 with aqueous sodium hydroxide (specific gravity 1.5) and extracted with dichloromethane (3×150 ml). The combined extracts were filtered through silica (100 g) and the solvent removed by distillation from the filtrate. The residue was dissolved in hydrochloric acid (5M, 100 ml), washed with diethyl ether (2×100 ml) and the washings were discarded. The aqueous layer was neutralised with aqueous sodium hydroxide (5M) and extracted with diethyl ether (2×100 ml). The combined extracts were dried over magnesium sulphate and the solvent was removed by distillation to give a mixture of the novel compounds 5'-fluoro-2'-(methylamino)acetophenone and 5'-chloro-2'-(methylamino)acetophenone.

(c) The mixture of 5'-fluoro-2'-(methylamino)acetophenone and 5'-chloro-2'-(methylamino)acetophenone was then converted to a mixture of 6-fluoro-1-methyl-4-oxo-1,4-dihydroquinol-3-yl methanesulphonate and 6-chloro-1-methyl-4-oxo-1,4-dihydroquinol-3-yl methanesulphonate respectively in a manner analogous to that described in Example 7b-f. The mixture was separated by flash chromatography on a silica gel column eluted with dichloromethane:methanol (40:1) to give the novel compounds 6-fluoro-1-methyl-4-oxo-1,4-dihydroquinol-3-yl methanesulphonate, m.p. 188°–189° and 6-chloro-1-methyl-4-oxo-1,4-dihydroquinol-3-yl methanesulphonate, m.p. 194°–196°.

EXAMPLE 28

(a) A solution of N-methylaniline (5.43 ml) in toluene (60 ml) was added dropwise over 20 minutes to a stirred solution of boron trichloride (1M, 50 ml) in hexane at 0 to 5° under nitrogen. Chloroacetonitrile (3.8 ml) and then aluminium trichloride (7.34 g) were added and the mixture was stirred and heated under reflux overnight. The mixture was cooled to 20° and hydrochloric acid (2M, 100 ml) added. The mixture was heated at 100° for 30 minutes, then cooled to 20° and adjusted to pH 3 to 4 with aqueous sodium hydroxide (5M, 50 ml). The mixture was extracted with dichloromethane (2×400 ml) and the combined extracts were dried over magnesium sulphate. The solvent was removed by evaporation under reduced pressure and the residue purified by flash chromatography on a silica gel column eluted with dichloromethane to give 2-chloro-2'-(methylamino)acetophenone, m.p. 65°–68°.

(b) A mixture of formic acid (2.3 ml) and acetic anhydride (3.6 ml) was heated at 50 to 60° for 2 hours, cooled to 0 to 5° and dichloromethane (10 ml) added. A solution of 2-chloro-2'-(methylamino)acetophenone (1.6 g) in dichloromethane (25 ml) was added and the solution then stirred at 10°–20° for 3 hours. The solution was cooled to 0 to 5° and water (50 ml) followed by aqueous sodium bicarbonate (1M, 50 ml) was added. The layers were separated and the aqueous layer was extracted with dichloromethane (50 ml). The combined dichloromethane layer and extract were dried over magnesium sulphate and the solvent was removed by distillation to give the novel compound 2'-(2-chloro-acetyl)-N-methylformanilide in the form of an oil.

(c) The solution of 2'-(2-chloroacetyl)-N-methylformanilide may be reacted with benzoic acid by a method analogous to that of Example 2(d) to give the novel compound 2-[2-(N-methylformamido)phenyl]-2oxoethyl benzoate.

(d) 2-[2-(N-methylformamido)phenyl]-2-oxoethyl benzoate may be treated by a method analogous to that of Example 1(e), 1(f) and 1(g) to give the novel compound 1-methyl-4-oxo-1,4-dihydroquinol-3-yl methanesulphonate.

EXAMPLE 29

A mixture of 2'-chloroacetophenone (309 g), industrial methylated spirit (252 ml), methylamine (33% w/w solution in industrial methylated spirit, 1085 ml) and copper lining powder (2.7 g) was stirred in a sealed pressure vessel for 3 hours at 80° C. The reaction vessel was allowed to cool to 40° and the mixture was washed out of the vessel with industrial methylated spirit (60 ml). The combined reaction mixture and washing were stirred at 50 to 55°, a solution of sodium sulphide trihydrate (6.6 g) in water (45 ml) was added dropwise and the stirring and heating were continued for 15 minutes. The mixture was filtered through diatomaceous earth (sold under the trade name HYFLO SUPERCEL) and the filter bed washed with industrial methylated spirit (300 ml). The combined filtrate and washing were evaporated under reduced pressure to give an oil which was added to hydrochloric acid (5M, 900 ml) and then stirred and heated under reflux for 2 hours. The mixture was cooled to 30°, washed with hexane (2×990 ml) and then adjusted to pH 2 to 3 by addition of aqueous sodium hydroxide (5M, 750 ml) whilst maintaining the temperature at 30 to 35°. The mixture was then extracted with dichloromethane (990 ml) and the extract evaporated under reduced pressure to give the novel compound 2'-(methylamino)acetophenone, m.p. 34°–35°.

(b) 2'-(methylamino)acetophenone may be treated by a method analogous to that of Example 2be to give the novel compound 1-methyl-4-oxo-1,4-dihydroquinol-3-yl methanesulphonate.

EXAMPLE 30

(a) A solution of 4'-methoxy-3'-methylacetanilide (71g) in dry tetrahydrofuran (350 ml) was added over 45 minutes to a stirred suspension of sodium hydride (19 g of a 50% dispersion in mineral oil) in dry tetrahydrofuran (250 ml) under nitrogen. The stirred mixture was heated under reflux for 10 minutes, then cooled to 0 to 5° and iodomethane (25 ml) added dropwise over 10 minutes. After the mixture was stirred and heated under reflux for a further 2 hours, the mixture was cooled to ambient temperature and industrial methylated spirit (50 ml) followed by aqueous ammonia (specific gravity 0.88, 50 ml) were added. After 30 minutes, solvent was removed by evaporation, water (500 ml) added to the residue and the mixture extracted with ethyl acetate (3×300 ml). The combined extracts were washed with aqueous sodium metabisulphite (10% w/w, 2×300 ml), dried over magnesium sulphate, and the solvent removed by evaporation. The residue was triturated with petroleum ether (b.p. 40°-60°) and the solid collected by filtration to give the novel compound 4'-methoxy-3'-methyl-N-methylacetanilide, m.p. 65°-66°.

(b) A mixture of 4'-methoxy-3'-methyl-N-methylacetanilide (53 g), sodium hydroxide (22 g), water (75 ml) and industrial methylated spirit (200 ml) was heated under reflux for 36 hours. Solvent was removed by evaporation, water (350 ml) was added to the residue and the mixture extracted with diethyl ether (2×300 ml). The combined extracts were washed with water (250 ml), dried over magnesium sulphate and the solvent was removed by evaporation to give the novel compound 4-methoxy-3-methyl-N-methylaniline in the form of an oil.

(c) 4-Methoxy-3-methyl-N-methylaniline (30.2 g) is added dropwise to a stirred solution of boron trichloride (26 g) in toluene (100 ml) cooled to 0 to 5°. Chloroacetonitrile (19.9 g) and then titanium tetrachloride (26.8 ml) are added and the mixture is heated under reflux for 6 hours. After cooling to ambient temperature, hydrochloric acid (2M, 500 ml) is added and the mixture then heated to 80° for 30 minutes. The mixture is cooled to ambient temperature, sodium hydroxide (2M) is added to pH 3 and the mixture then extracted with dichloromethane (3×300 ml). The combined extracts are washed with water (100 ml) and dried over magnesium sulphate. The solvent is removed by distillation and the residue purified to give the novel compound 2-chloro-5'-methoxy-4'-methyl-2'-(methylamino)acetophenone.

(d) 2-Chloro-5'-methoxy-4'-methyl-2'-(methylamino)acetophenone (10 g) is added at ambient temperature to a stirred mixture of acetic anhydride (23 ml) and formic acid (16 ml), previously stirred at 55° for a 1hour, and the resultant mixture is stirred for 2 hours at 20°. Water (80 ml) followed by aqueous sodium hydroxide (specific gravity 1.5, 60 ml) are added, whilst maintaining the temperature below 10°. The mixture is then extracted with dichloromethane to give a solution of 2'-(2-chloroacetyl)-4'-methoxy-5'-methyl-N-methyl-formanilide.

(e) The solution of 2'-(2-chloroacetyl)-4'-methoxy-5'-methyl-N-methylformanilide may be reacted with benzoic acid by a method analogous to that of Example 2(d) to give the novel compound 2-[5-methoxy-4-methyl-2-(N-methylformamido)phenyl]-2-oxoethyl benzoate.

(f) 2-[5-Methoxy-4-methyl-2-(N-methylformamido)phenyl]-2-oxoethyl benzoate may be treated by a method analogous to that of Example 1(e), 1(f) and 1(g) to give the novel compound 6-methoxy-1,7-dimethyl-4-oxo-1,4-dihydroquinol-3-yl methanesulphonate.

EXAMPLE 31

In the preparation of capsules, 10 parts by weight of active compound and 240 parts by weight of lactose are de-aggregated and blended. The mixture is filled into hard gelatin capsules, each capsule containing 10 mg of active compound.

EXAMPLE 32

Tablets are prepared from the following ingredients.

|  | Parts by weight |
| --- | --- |
| Active compound prepared as in Example 1 | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets containing 10 mg active compound.

EXAMPLE 33

Tablets are prepared by the method of Example 32. The tablets are enteric coated in a conventional manner using a solution of 20% cellulose acetate phthalate and 3% diethyl phthalate in ethanol:dichloromethane (1:1).

EXAMPLE 34

In the preparation of suppositories, 100 parts by weight of active compound is incorporated in 1300 parts by weight of triglyceride suppository base and the mixture formed into suppositories each containing 100 mg of active ingredient.

EXAMPLE 35

In the preparation of capsules, 50 parts by weight of active compound and 300 parts by weight of lactose are de-aggregated and blended. The mixture is filled into hard gelatin capsules, each capsule containing 50 mg of active compound

We claim:

1. A compound of formula I

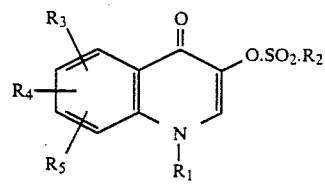

in which $R_1$ is lower alkyl; $R_2$ is lower alkyl; and $R_3$ and $R_4$, which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo and $R_5$ pl is hydrogen.

2. A compound as claimed in claim 2 in which $R_1$ is alkyl having 1 to 4 carbon atoms; $R_2$ is alkyl having 1 to 4 carbon atoms; and $R_3$ and $R_4$, which may be the same or different, are hydrogen, lower alkyl having 1 to 4 carbon atoms, lower alkoxy having 1 to 4 carbon atoms, lower alkylthio having to 4 carbon atoms, lower alkylsulphinyl having 1 to 4 carbon atoms, lower alkylsulphonyl having 1 to 4 carbon atoms, halo, fluorinated lower alkyl having 1 to 4 carbon atoms, fluorinated lower alkoxy having 1to 4 carbon atoms, cyano, phenyl or phenyl substituted by 1 or 2 groups independently selected from alkyl having 1 to 4 carbon atoms, alkoxy having to 4 carbon atoms and halo.

3. A compound as claimed in claim 2 in which $R_1$ is methyl or ethyl; $R_2$ is methyl, ethyl, isopropyl or butyl; and $R_3$ and $R_4$, which may be the same or different, are hydrogen, methyl, methoxy, methylthio, methylsulphinyl, methylsulphonyl, fluoro, chloro, trifluoromethyl, trifluoromethoxy, 2,2,2-trifluoroethoxy, cyano or phenyl.

4. A compound as claimed in claim 3 in which $R_1$ is methyl or ethyl; $R_2$ is methyl; and $R_3$ and $R_4$, which may be the same or different, are hydrogen, methyl, methoxy, methylthio, methylsulphinyl, fluoro, chloro, trifluoromethyl, trifluoromethoxy or cyano.

5. A compound as claimed in claim 4 in which $R_4$ is hydrogen.

6. A compound as claimed in claim 1 of formula II

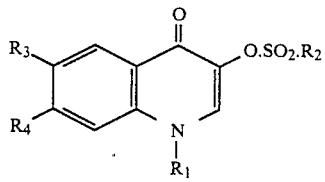

in which $R_1$ is lower alkyl; $R_2$ is lower alkyl; and $R_3$ (in the 6-position) and $R_4$ (in the 7-position), which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo.

7. A compound as claimed in claim 6 in which $R_1$ is alkyl having 1 to 4 carbon atoms; $R_2$ is alkyl having 1 to 4 carbon atoms; and $R_3$ and $R_4$, which may be the same or different, are hydrogen, alkyl having 1 to 4 carbon atoms, alkoxy having to 4 carbon atoms, alkylthio having 1 to 4 carbon atoms, alkylsulphinyl having 1 to 4 carbon atoms, alkylsulphonyl having 1 to 4 carbon atoms, halo, fluorinated alkyl having 1 to 4 carbon atoms, fluorinated alkoxy having 1 to 4 carbon atoms, cyano, phenyl or phenyl substituted by 1 or 2 groups independently selected from alkyl having 1 to 4 carbon atoms, alkoxy having 1 to 4 carbon atoms and halo.

8. A compound as claimed in claim 7 in which $R_1$ is methyl or ethyl, $R_2$ is methyl and $R_3$ and $R_4$ are each independently selected from hydrogen, alkyl having 1 to 4 carbon atoms, alkoxy having 1 to 4 carbon atoms and halo.

9. A compound is claimed in claim 6 in which $R_1$ is methyl or ethyl; $R_2$ is methyl, ethyl, isopropyl or butyl; and one of $R_3$ and $R_4$ is hydrogen and the other is hydrogen, methyl, methoxy, methylthio, methylsulphinyl, methylsulphonyl, fluoro, chloro, trifluoromethyl, trifluoromethoxy, 2,2,2-trifluoroethoxy, cyano or phenyl.

10. A compound as claimed in claim 9 in which $R_1$ and $R_2$ are methyl and one of $R_3$ and $R_4$ is hydrogen and the other is hydrogen, methyl, methoxy, methylthio, methylsulphinyl, fluoro, chloro, trifluoromethyl, trifluoromethoxy or cyano.

11. A compound as claimed in claim 10 in which $R_3$ is hydrogen and R is hydrogen, methyl, methoxy, methylthio, fluoro, chloro, trifluoromethyl or trifluoromethoxy.

12. 1-Methyl-4-oxo-1,4-dihydroquinol-3-yl methanesulphonate.

13. 7-Fluoro-1-methyl-4-oxo-1,4-dihydroquinol-3-yl methanesulphonate.

14. A compound as claimed in claim 10 in which $R_3$ is chloro or fluoro and $R_4$ is hydrogen.

15. 6-Fluoro-1-methyl-4-oxo-1,4-dihydroquinol-3-yl methanesulphonate.

16. An antihypertensive composition which comprises a compound of formula I

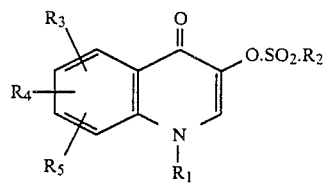

in which $R_1$ is lower alkyl; $R_2$ is lower alkyl; and $R_3$, $R_4$ and $R_5$ which may be the same or different, are hydrogen, lower alkyl, lower alkoxy, lower alkylthio, lower alkylsulphinyl, lower alkylsulphonyl, halo, halogenated lower alkyl, halogenated lower alkoxy, cyano, phenyl or phenyl substituted by 1 or 2 groups independently selected from lower alkyl, lower alkoxy and halo, and $R_5$ is hydrogen; together with a pharmaceutically acceptable carrier.

17. A composition as claimed in claim 16 in unit dosage form.

18. A composition as claimed in claim 16 or claim 17 in the form of a tablet, capsule or suppository.

19. A composition as claimed in any one of claims 16 to 18 wherein the compound of formula I is a compound as claimed in any one of claims 1 to 15.

20. A composition as claimed in any one of claims 16 to 19 in which the compound of formula I is 1-methyl-4-oxo-1,4-dihydroquinol-3-yl methanesulphonate.

21. A composition as claimed in any one of claims 16 to 19 in which the compound of formula I is 7-fluoro-1-methyl-4-oxo-1,4-dihydroquinol-3-yl methanesulphonate.

22. A method of greating hypertension in a manual in need of such treatment which comprises the administration of a compound of formula I as claimed in anmyt one of claims 1 to 15.

* * * * *